United States Patent [19]

Jacobsen et al.

[11] Patent Number: 5,834,393

[45] Date of Patent: Nov. 10, 1998

[54] ADDUCT OF AN ORGANOMETAL COMPOUND AND A COMPATIBLE ANION, SUPPORTED CATALYST COMPONENT SUPPORTED CATALYST PROCESSES FOR THE PREPARATION THEREOF

[75] Inventors: Grant Berent Jacobsen, 4542 BM Hoek; Peter Wijkens, 3525 VR Utrecht; Johann T. B. H. Jastrzebski, 3731 XA De Bilt; Gerard Van Koten, 3735 CN Den Dolder, all of Netherlands

[73] Assignee: The Dow Chemical Company, Midland, Mich.

[21] Appl. No.: 610,647

[22] Filed: Mar. 4, 1996

Related U.S. Application Data

[63] Continuation-in-part of Ser. No. 402,437, Mar. 10, 1995, abandoned.

[51] Int. Cl.[6] .............................. B01J 31/00; B01J 21/02; C08F 4/02; C08F 4/60
[52] U.S. Cl. ........................ 502/152; 502/202; 502/153; 502/129; 502/131; 502/132; 502/133; 502/118; 502/125; 502/102; 502/103; 502/117
[58] Field of Search ...................... 502/114, 116, 502/117, 118, 119, 120, 121, 122, 123, 124, 125, 130, 132, 133, 153, 152, 202

[56] References Cited

U.S. PATENT DOCUMENTS

| | | | |
|---|---|---|---|
| 4,542,119 | 9/1985 | Hsu et al. | 502/153 |
| 4,954,616 | 9/1990 | Callens et al. | 530/333 |
| 5,015,749 | 5/1991 | Schmidt et al. | 556/179 |
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,132,380 | 7/1992 | Stevens et al. | 526/126 |
| 5,206,197 | 4/1993 | Campbell, Jr. | 502/117 |
| 5,278,119 | 1/1994 | Tuner et al. | 502/117 |
| 5,296,433 | 3/1994 | Siedle et al. | 502/117 |
| 5,330,948 | 7/1994 | Marks et al. | 502/117 |
| 5,374,696 | 12/1994 | Rosen et al. | 526/126 |
| 5,387,568 | 2/1995 | Ewen et al. | 502/117 |
| 5,407,884 | 4/1995 | Turner et al. | 502/117 |
| 5,427,991 | 6/1995 | Turner | 502/103 |
| 5,447,895 | 9/1995 | Marks et al. | 502/117 |
| 5,466,647 | 11/1995 | Sangokoya | 502/113 |
| 5,480,848 | 1/1996 | Geerts | 502/152 |
| 5,587,439 | 12/1996 | DiMaio | 502/124 |
| 5,643,847 | 7/1997 | Walzer, Jr. | 502/117 |
| 5,663,249 | 9/1997 | Ewen et al. | 502/152 |
| 5,721,183 | 2/1998 | Neithamer | 502/202 |

FOREIGN PATENT DOCUMENTS

| | | |
|---|---|---|
| 0416815 | 3/1991 | European Pat. Off. . |
| 9109882 | 7/1991 | WIPO . |
| 9403506 | 2/1994 | WIPO . |
| 9403509 | 2/1994 | WIPO . |
| 9500526 | 1/1995 | WIPO . |

OTHER PUBLICATIONS

The Role of Non–Coordinating Anions in Homogeneous Olefin Polymerization, Makromol. Chem., Symp. vol. 66, pp. 215–224 (1993), A. R. Siedle et al.

Neville, Roy G., "Synthesis of 4–(2,3–Epoxypropolxy)phenyltrimethylsilane", J. Org. Chem., vol. 25, pp. 1063–1064 (1960).

*Primary Examiner*—Glenn Caldarola
*Assistant Examiner*—J. Pasterczyk
*Attorney, Agent, or Firm*—John H. Roberts

[57] ABSTRACT

A supported catalyst component comprising (a) a support material, an organometal compound, and (b) an activator compound comprising b.1) a cation which is capable of reacting with a transition metal metallocene compound to form a catalytically active transition metal complex, and b.2) a compatible anion having up to 100 nonhydrogen atoms and containing at least one substituent comprising an active hydrogen moiety; a supported catalyst comprising the supported catalyst component and a transition metal compound; process for making the same; an addition polymerization process using the supported catalyst; complex compounds, and a method for preparing the same. In the mixture of the support material, the organometal compound, and the ionic activator compound, the organometal compound reacts with residual hydroxyl groups on the support, forming a hydrocarbon byproduct and an organometal compound bound to the support, and the active hydrogen on the anion of the activator reacts further with the bound organometal compound to form a further hydrocarbon byproduct. The order of addition is immaterial as long as these are the three essential ingredients added in the formation of the support-bound activator complex.

24 Claims, No Drawings

ADDUCT OF AN ORGANOMETAL COMPOUND AND A COMPATIBLE ANION, SUPPORTED CATALYST COMPONENT SUPPORTED CATALYST PROCESSES FOR THE PREPARATION THEREOF

CROSS-REFERENCE TO RELATED APPLICATION

This application is a continuation-in-part application of application Ser. No. 08/402,437, filed Mar. 10, 1995, now abandoned.

FIELD OF THE INVENTION

This invention relates to a supported catalyst component comprising a support material, an organometal compound, and an activator compound, to a supported catalyst comprising said supported catalyst component and a transition metal compound, to a process for preparing such a supported catalyst component and catalyst, to a polymerization process using such a supported catalyst, to complex compounds for use as activator compounds, and to a process for making such complex compounds.

BACKGROUND OF THE INVENTION

Homogeneous or non-supported ionic transition metal catalysts are known for their high catalytic activity in olefin polymerizations. Under polymerization conditions where polymer is formed as solid particles, these homogeneous (soluble) catalysts form polymer deposits on reactor walls and stirrers which deposits should be removed frequently as they prevent an efficient heat-exchange necessary for cooling the reactor contents and cause excessive wear of the moving parts in the reactor. The polymers produced by these soluble catalysts further have a low bulk density which limits the commercial utility of both the polymer and the process. In order to solve these problems, several supported ionic catalysts have been proposed for use in particle forming polymerization processes.

WO-91/09882 describes a supported ionic metallocene catalyst prepared by combining i) a bis(cyclopentadienyl) metal compound containing at least one ligand capable of reacting with a proton, ii) an activator component comprising a cation capable of donating a proton and a bulky, labile anion capable of stabilizing the metal cation formed as a result of reaction between the metal compound and the activator component, and iii) a catalyst support material. The support material may be subjected to a thermal or chemical dehydration treatment. In some of the examples triethylaluminum was added for this purpose. The maximum bulk density reported in the examples of WO91/09882 is 0.17 g/cm$^3$ and the catalyst efficiency is not satisfactory.

WO-94/03506 describes a supported ionic catalyst prepared by combining i) a monocyclopentadienyl metal compound, ii) an activator component comprising a cation which will irreversibly react with at least one ligand contained in said metal compound and an anion, said anion being a chemically stable non-nucleophilic anionic complex, and iii) a catalyst support material, optionally followed by prepolymerizing said supported catalyst system with an olefinic monomer. The support material may be treated with a hydrolyzable organoadditive, preferably a Group 13 alkyl compound such as triethylaluminum. The catalyst efficiencies obtained in WO-94/03506, however, are very low. WO-94/03509 suggests the use of supported ionic catalysts such as described in WO-94/03506 for use in a gas phase polymerization process.

WO-93/21238 discloses tris(pentafluorophenyl)borane complexes of water, alcohols, mercaptans, silanols, oximes, and mixtures thereof. These neutral complexes may be converted to acidic salts of their conjugate bases by reaction with amines. These complexes and acidic salts thereof together with Group 4 transition metal compounds, especially metallocenes, were disclosed as being useful as homogeneous olefin polymerization catalysts.

WO-93/11172 relates to polyionic transition metal catalyst compositions. It is suggested that polyanionic activators are used to prepare a catalyst system of enhanced performance by immobilizing the catalyst on a support material. It is believed, however, that the teachings in WO-93/11172 do not suffice for preparing a supported catalyst based on surface-hydroxyl groups containing support materials. FIG. 1, Formula 3 and page 26, line 25 suggest so-called alcohol-functionalized synthons to be used in making the polyanionic activators. Several methods are suggested to make catalyst supports based on polyanionic activators made from alcohol-functionalized synthons, as discussed below. In a first method (page 26, line 32-36 and FIG. 1 Formula 6) the alcohol functionalized synthon is converted into silylhalide analogs by treatment with $R'_j SiCl_{4-j}$ (j=0 to 3). As indicated therein, HCl is liberated which should be adsorbed by a tertiary amine. This, however, will give the by-product $R_3NHCl$. The ammonium chloride thus formed is not a suitable activator compound for a transition metal catalyst because the chloride anion is not a non-coordinating anion which is typically required for such type of catalyst, and the catalyst thus made will not have substantial catalyst activity. The compound of Formula 6 may be reacted with a hydroxylated substrate such as silica gel, alumina or metal oxides (page 34, lines 25–28 and FIG. 1 route C). When using the compound of Formula 6 equivalents of HCl may be liberated, which compound and the possibly suggested by-product ammonium chloride will provide catalyst systems having only insignificant catalytic activities.

On page 32, lines 11–18 further methods are suggested for making catalyst supports from the alcohol-functionalized synthons: acid catalyzed dehydration of hydroxylated surfaces (such as amorphous silica), and esterification or transesterification of discrete or polymeric materials containing more than one carboxylic acid or ester per molecule, polymer chain or particle. All such reactions liberate water, which is a poison for transition metal catalysts.

A further method is described on page 34, line 34 to page 35, line 37 and page 37, line 16 to page 38, line 14, as well as in FIG. 8. According to that method, a support material is provided with anionic functionalities by reacting a silane halide or silane alkoxide coupling agent with a hydroxylated surface of silica. On page 35, lines 33–37 it is suggested to mask or protect reactive functionalities such as hydroxyl functions (on the silica). On page 37, lines 20–31 this is further explained and it is indicated that part of the hydroxyl functions can be masked and the remaining part can be converted into said anionic functionalities. This would enable varying or adjusting the concentration of (ultimately) anionic functionalities. A mixture of bromophenyl silane trimethoxy and phenylsilane trimethoxy is mentioned in this context. Accordingly, the hydroxyl functionalities which are masked or protected are not used for preparing anionic functionalities. Besides, using silane halides or silane alkoxides to react with surface hydroxyl groups would give as by-product hydrogen halides and alcohols which are catalyst poisons. Accordingly, none of the suggested methods are believed to give effective supported catalysts.

It would be desirable to provide a supported catalyst and supported catalyst component thereof, and a polymerization process that is capable of producing polymers at good catalyst efficiencies, thereby avoiding or reducing some of the disadvantages occurring in the prior art.

SUMMARY OF THE INVENTION

In one aspect of the present invention there is provided a supported catalyst component comprising (a) a support material, an organometal compound wherein the metal is selected from Groups 2–13 of the Periodic Table of Elements, germanium, tin, and lead, and (b) an activator compound comprising b.1) a cation which is capable of reacting with a transition metal compound to form a catalytically active transition metal complex, and b.2) a compatible anion having up to 100 nonhydrogen atoms and containing at least one substituent comprising an active hydrogen moiety.

In a second aspect there is provided a supported catalyst comprising the supported catalyst component of the invention and (c) a transition metal compound containing a substituent capable of reacting with activator compound (b) to thereby form a catalytically active transition metal complex.

In a further aspect the invention provides a process for preparing a supported catalyst component comprising combining a support material (a), an organometal compound wherein the metal is selected from Groups 2–13 of the Periodic Table of the Elements, germanium, tin, and lead, and an activator compound (b) comprising b.1) a cation which is capable of reacting with a transition metal compound to form a catalytically active transition metal complex, and b.2) a compatible anion having up to 100 nonhydrogen atoms and containing at least one substituent comprising an active hydrogen moiety.

In another aspect of the invention there is provided a process for preparing a supported catalyst comprising the process for making the supported catalyst component of the present invention and the further step of adding a transition metal compound (c) containing a substituent capable of reacting with activator compound (b) to thereby form a catalytically active transition metal complex.

In yet a further aspect the present invention provides an adduct of an organometal compound wherein the metal is selected from Groups 2–13 of the Periodic Table of the Elements, germanium, tin, and lead, and an activator compound comprising b.1) a cation which is capable of reacting with a transition metal compound to form a catalytically active transition metal complex and, b.2) a compatible anion having up to 100 nonhydrogen atoms and containing at least one substituent comprising an active hydrogen moiety, obtained by combining the organometal compound and the activator compound in a suitable diluent or solvent, optionally followed by removing the solvent or diluent.

In yet another aspect the invention provides an addition polymerization process wherein one or more addition polymerizable monomers are contacted with a supported catalyst according to the present invention under addition polymerization conditions.

In yet a further aspect there is provided a complex compound comprising a charge balancing cation, and a compatible anion corresponding to Formula (I):

  (I)

wherein:
M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion having from 1 to 20 carbons with the proviso that in not more than one occurrence is Q halide;

G is a polyvalent hydrocarbon radical, having r+1 valencies, bonded to M' and T;

T is O, S, NR, or PR, wherein R is a hydrocarbon radical, a trihydrocarbyl silyl radical, a trihydrocarbyl germyl radical, or hydrogen;

Bl is hydrogen H or a protecting group;

m is an integer from 1 to 7;

n is an integer from 0 to 7;

q is 1;

r is an integer from 1 to 3;

z is an integer from 1 to 8;

d is an integer from 1 to 7; and n+z−m=d.

According to a further aspect the present invention provides a method for preparing a complex compound containing an anion corresponding to the Formula (I).

  (I)

wherein:
M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion having from 1 to 20 carbons with the proviso that in not more than one occurrence is Q halide;

G is a polyvalent hydrocarbon radical, having r+1 valencies, bonded to M' and T;

T is O, S, NR, or PR, wherein R is a hydrocarbyl radicals a trihydrocarbyl silyl radical, a trihydrocarbyl germyl radical or hydrogen;

Bl is hydrogen H or a protecting group;

m is an integer from 1 to 7;

n is an integer from 0 to 7;

q is an integer of 0 or 1;

r is an integer from 1 to 3;

z is an integer from 1 to 8;

d is an integer from 1 to 7; and n+z−m=d; and a charge balancing cation;

in which complex compound the anion and cation are contained in such relative quantities to provide a neutral compound, comprising the steps of combining in a suitable solvent or diluent a compound $M'^{m+}Q_m$ with a compound of the formula $Z^1(G_q(T-Bl)_r)$, wherein $Z^1$ is $[M*X]^+$ or $[M]+$ and $M*$ is a group 2 element, $M**$ is a group 1 element and X is halogen, G, T, Bl, q, and r have the same meaning as given for Formula (I), optionally followed by recovering the product complex.

DETAILED DESCRIPTION OF THE INVENTION

All references herein to elements or metals belonging to a certain Group refer to the Periodic Table of the Elements published and copyrighted by CRC Press, Inc., 1989. Also any reference to the Group or Groups shall be to the Group or Groups as reflected in this Periodic Table of the Elements using the IUPAC system for numbering groups.

Surprisingly, it has been found that a complex compound that contains at least one substituent comprising an active hydrogen moiety as specified herein, can be attached to the support and is capable of activating transition metal catalysts typically employed in addition polymerization processes. This is surprising, as it is known, that active hydrogen-containing compounds tend to deactivate typical transition metal catalysts, especially those transition metal catalysts containing a cyclopentadienyl moiety or a derivative thereof. The present supported catalysts can be employed to produce polymers at satisfactory catalyst efficiencies.

An additional benefit is that the formation of polymer deposits at reactor walls and other moving parts in the reactor is avoided; and the polymers are in the form of free flowing powder or particles, when a particle forming polymerization process, such as a slurry or gas phase polymerization process, is employed so that the polymers can be easily transported, and that polymers of improved bulk density are obtained in such particle forming polymerization processes. According to the present invention improved bulk densities, for ethylene based polymers and interpolymers, are preferably bulk densities of at least about 0.20 $g/cm^3$, and more preferably of at least about 0.25 $g/cm^3$. In the supported catalyst components and catalysts, the activating complexes are well dispersed throughout the pore structure of the porous support material, which is one of the important factors for maintaining both an extended period and a high level of catalyst efficiency. During the formation of polymer on the supported catalyst particles, the particles tend to fragment and thus make fresh surface available for polymer growth. The presence of catalytically active groups on such fresh surface is very desirable for providing good catalyst efficiencies and polymer morphology.

Suitable support materials for use in the present invention include porous resinous materials, for example, polyolefins such as polyethylenes and polypropylenes or copolymers of styrene-divinylbenzene, and solid inorganic oxides including oxides of Group 2, 3, 4, 13, or 14 metals, such as silica, alumina, magnesium oxide, titanium oxide, thorium oxide, as well as mixed oxides of silica. Suitable mixed oxides of silica include those of silica and one or more Group 2 or 13 metal oxides, such as silica-magnesia or silica-alumina mixed oxides. Silica, alumina, and mixed oxides of silica and one or more Group 2 or 13 metal oxides are preferred support materials. Preferred examples of such mixed oxides are the silica-aluminas. The most preferred support material is silica. The shape of the silica particles is not critical and the silica may be in granular, spherical, agglomerated, fumed or other form. Suitable silicas include those that are available from Grace Davison (division of W. R. Grace & Co.) under the designations SD 3216.30, SP-9-10046, Davison Syloid 245, Davison 948 and Davison 952, from Degussa AG under the designation Aerosil 812, and from Crossfield under the designation ES 70X.

Support materials suitable for the present invention preferably have a surface area as determined by nitrogen porosimetry using the B.E.T. method from 10 to about 1000 $m^2/g$, and preferably from about 100 to 600 $m^2/g$. The pore volume of the support, as determined by nitrogen adsorption, is typically up to 5 $cm^3/g$, advantageously between 0.1 and 3 $cm^3/g$, preferably from about 0.2 to 2 $cm^3/g$. The average particle size is not critical but typically is from 0.5 to 500 $\mu m$, preferably from 1 to 200 $\mu m$, more preferably to 100 $\mu m$.

The support material may be subjected to a heat treatment and/or chemical treatment to reduce the water content or the hydroxyl content of the support material. Both dehydrated support materials and support materials containing small amounts of water can be used. Typical thermal pretreatment are carried out at a temperature from 30° C. to 1000° C. for a duration of 10 minutes to 50 hours in an inert atmosphere or under reduced pressure. Typical support materials have a surface hydroxyl content of from 0.1 micromol, preferably from 5 micromol, more preferably from 0.05 mmol to not more than 5 mmol hydroxyl groups per g of solid support, more preferably from 0.5 to 2 mmol per gram. The hydroxyl content can be determined by known techniques, such as infrared spectroscopy and titration techniques using a metal alkyl or metal hydroxide, for example, adding an excess of dialkyl magnesium to a slurry of the solid support and determining the amount of dialkyl magnesium remaining in solution via known techniques. This latter method is based on the reaction of S—OH+$MgR_2$+S—OMgR+RH, wherein S is the solid support.

The support material is treated with the organometal compound. Suitable organometal compounds are those comprising metals of Groups 2–13, germanium, tin, and lead, and at least two substituents selected from hydride, hydrocarbyl radicals, trihydrocarbyl silyl radicals, and trihydrocarbyl germyl radicals. Additional substituents preferably comprise one or more substituents selected from hydride, hydrocarbyl radicals, trihydrocarbyl substituted silyl radicals, trihydrocarbyl substituted germyl radicals, and hydrocarbyl-, trihydrocarbyl silyl- or trihydrocarbyl germyl-substituted metalloid radicals.

The recitation "metalloid", as used herein, includes nonmetals such as boron, phosphorus and the like which exhibit semi-metallic characteristics.

Examples of such organometal compounds include organomagnesium, organozinc, organoboron, organoaluminum, organogermanium, organotin, and organolead compounds, and mixtures thereof. Further suitable organometal compounds are alumoxanes. Preferred examples are alumoxanes and compounds represented by the following formulae: $MgR^1_2$, $ZnR^1_2$, $BR^1_xR^2_y$, $AlR^1_xR^2_y$, wherein $R^1$ independently each occurrence is hydride, a hydrocarbyl radical, a trihydrocarbyl silyl radical, a trihydrocarbyl germyl radical, or a trihydrocarbyl-, trihydrocarbyl silyl-, or trihydrocarbyl germyl-substituted metalloid radical, $R^2$ independently is the same as $R^1$, x is 2 or 3, y is 0 or 1 and the sum of x and y is 3, and mixtures thereof. Examples of suitable hydrocarbyl moieties are those having from 1 to 20 carbon atoms in the hydrocarbyl portion thereof, such as alkyl, aryl, alkaryl, or aralkyl. Preferred radicals include methyl, ethyl, n- or i-propyl, n-, s- or t-butyl, phenyl, and benzyl. Preferably, the aluminum component is selected from the group consisting of alumoxane and aluminum compounds of the formula Al $R^1_x$ wherein $R^1$ in each occurrence independently is hydride or a hydrocarbyl radical having from 1 to 20 carbon atoms, and x is 3. Suitable trihydrocarbyl aluminum compounds are trialkyl or triaryl aluminum compounds wherein each alkyl or aryl group has from 1 to 10 carbon atoms, or mixtures thereof, and preferably trialkyl aluminum compounds such as trimethyl, triethyl, tri-isobutyl aluminum.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (–Al(R)—O)$_m$, for a cyclic alumoxane, and R$_2$Al—O(—Al(R)—O)$_m$—AlR$_2$, for a linear compound, wherein R independently in each occurrence is a C$_1$–C$_{10}$ hydrocarbyl, preferably alkyl, or halide and m is an integer ranging from 1 to about 50, preferably at least about 4. Alumoxanes are typically the reaction products of water and an aluminum alkyl, which in addition to an alkyl group may contain halide or alkoxide groups. Reacting several different aluminum alkyl compounds, such as, for example, trimethyl aluminum and tri-isobutyl aluminum, with water yields so-called modified or mixed alumoxanes. Preferred alumoxanes are methylalumoxane and methylalumoxane modified with minor amounts of other lower alkyl groups such as isobutyl. Alumoxanes generally contain minor to substantial amounts of starting aluminum alkyl compound.

The way in which the alumoxane is prepared is not critical. When prepared by the reaction between water and aluminum alkyl, the water may be combined with the aluminum alkyl in various forms, such as liquid, vapor, or solid, for example in the form of crystallization water. Particular techniques for the preparation of alumoxane type compounds by contacting an aluminum alkyl compound with an inorganic salt containing water of crystallization are disclosed in U.S. Pat. No. 4,542,199. In a particular preferred embodiment an aluminum alkyl compound is contacted with a regeneratable water-containing substance such as hydrated alumina, silica or other substance. This is disclosed in European Patent Application No. 338,044.

The supported catalyst component and supported catalyst of the present invention generally comprise a support material combined or treated with the organometal compound, preferably an aluminum component, and containing at least 0.1 micromol of organometal compound per g of support material, typically at least 5 micromole per g support material, advantageously at least 0.5 weight percent of the metal, preferably aluminum, expressed in gram of metal, preferably aluminum, atoms per g of support material. Preferably, the amount of metal, advantageously aluminum, is at least 2 weight percent, and generally not more than 40 weight percent, and more preferably not more than 30 weight percent. At too high amounts of metal, preferably aluminum, the supported catalyst becomes expensive. At too low amounts the catalyst efficiency goes down to drop below acceptable levels.

The supported catalyst component and supported catalyst of the present invention preferably contain a treated support material (a) comprising a support material and an alumoxane wherein not more than about 10 percent aluminum present in the treated support material is extractable in a one hour extraction with toluene of 90° C. using about 10 mL toluene per gram of pretreated support material. More preferably, not more than about 9 percent aluminum present in the supported catalyst component is extractable, and most preferably not more than about 8 percent. This is especially advantageous when the supported catalyst component or catalyst prepared therefrom is used in a polymerization process where a diluent or solvent is used which may extract non-fixed alumoxane from the support material. It has been found that when the amount of extractables is below the levels given above, the amount of alumoxane that can diffuse into the polymerization solvent or diluent, if used, is so low that no appreciable amount of polymer will be formed in the diluent, as compared to polymer formed on the support material. If too much polymer is formed in the diluent the polymer bulk density will decrease below acceptable levels and reactor fouling problems may occur.

The toluene extraction test is carried out as follows: About 1 g of supported catalyst component or supported catalyst, with a known aluminum content, is added to 10 mL toluene and the mixture is then heated to 90° C. under an inert atmosphere. The suspension is stirred well at this temperature for 1 hour. Then the suspension is filtered applying reduced pressure to assist in the filtration step. The solids are washed twice with about 3 to 5 mL toluene of 90° C. per gram of solids. The solids are then dried at 120° C. for 1 hour, and subsequently the aluminum content of the solids is measured. The difference between the initial aluminum content and the aluminum content after the extraction divided by the initial aluminum content and multiplied by 100%, gives the amount of extractable aluminum.

The aluminum content can be determined by slurrying about 0.5 g of supported catalyst component or supported catalyst in 10 mL hexane. The slurry is treated with 10 to 15 mL 6N sulfuric acid, followed by addition of a known excess of EDTA. The excess amount of EDTA is then back-titrated with zinc chloride.

Without wishing to be bound by any theory, it is believed that the activator compound used in the present invention reacts with the organometal compound, preferably aluminum component, through the active hydrogen-containing substituent. It is believed that a group R$^1$ of the organometal compound, preferably aluminum component, combines with the active hydrogen moiety of the activator compound to release a neutral organic compound, for example an alkane, or hydrogen gas thereby chemically coupling the metal, preferably aluminum atom with the activator compound residue. Thus the activator is believed to become chemically attached to the support material once the support material has been treated with the organometal compound or adduct of organometal compound and activator compound. Upon addition of the transition metal compound a supported catalyst is formed having improved properties.

The activator compound useful in the present invention contains a compatible anion having up to 100, and preferably up to 50 nonhydrogen atoms and having at least one substituent comprising an active hydrogen moiety. Preferred substituents comprising an active hydrogen moiety correspond to the formula

$$G_q(T\text{—}H)_r$$

wherein G is a polyvalent hydrocarbon radical, T is O, S, NR, or PR, wherein R is a hydrocarbyl radical, a trihydrocarbyl silyl radical, a trihydrocarbyl germyl radical, or hydrogen, H is hydrogen, q is 0 or 1, and preferably 1, and r is an integer from 1 to 3, preferably 1. Polyvalent hydrocarbon radical G has r+1 valencies, one valency being with a metal or metalloid of the Groups 5–15 of the Periodic Table of the Elements in the compatible anion, the other valency or valencies of G being attached to r groups T—H. Preferred examples of G include divalent hydrocarbon radicals such as: alkylene, arylene, aralkylene, or alkarylene radicals containing from 1 to 20 carbon atoms, more preferably from 2 to 12 carbon atoms. Suitable examples of G include phenylene, biphenylene, naphthylene, methylene, ethylene, 1,3-propylene, 1,4-butylene, phenylmethylene (—C$_6$H$_4$—CH$_2$—). The polyvalent hydrocarbyl portion G may be further substituted with radicals that do not interfere with the coupling function of the active hydrogen moiety. Preferred examples of such noninterfering substituents are alkyl, aryl, alkyl- or aryl-substituted silyl and germyl radicals, and fluoro substituents.

The group T—H in the previous formula thus may be an —OH, —SH, —NRH, or —PRH group, wherein R preferably is a C$_{1-18}$, preferably a C$_{1-10}$ hydrocarbyl radical or hydrogen, and H is hydrogen. Preferred R groups are alkyls, cycloalkyls, aryls, arylalkyls, or alkylaryls of 1 to 18 carbon atoms, more preferably those of 1 to 12 carbon atoms. The —OH, —SH, —NRH, or —PRH groups may be part of a larger functionality such as, for example, C(O)—OH, C(S)—SH, C(O)—NRH, and C(O)—PRH. Most preferably, the group T—H is a hydroxy group, —OH, or an amino group, —NRH.

Very preferred substituents $G_q(T—H)_r$ comprising an active hydrogen moiety include hydroxy- and amino- substituted aryl, aralkyl, alkaryl or alkyl groups, and most preferred are the hydroxyphenyls, especially the 3- and 4-hydroxyphenyl groups, hydroxytolyls, hydroxy benzyls (hydroxymethylphenyl), hydroxybiphenyls, hydroxynaphthyls, hydroxycyclohexyls, hydroxymethyls, and hydroxypropyls, and the corresponding amino-substituted groups, especially those substituted with —NRH wherein R is an alkyl or aryl radical having from 1 to 10 carbon atoms, such as for example methyl, ethyl, propyl, i-propyl, n-, i-, or t-butyl, pentyl, hexyl, heptyl, octyl, nonyl, and decyl, phenyl, benzyl, tolyl, xylyl, naphthyl, and biphenyl.

The compatible anion containing the substituent which contains an active hydrogen moiety, may further comprise a single Group 5–15 element or a plurality of Group 5–15 elements, but is preferably a single coordination complex comprising a charge-bearing metal or metalloid core, which anion is bulky. A compatible anion specifically refers to an anion which when functioning as a charge balancing anion in the catalyst system of this invention, does not transfer an anionic substituent or fragment thereof to the transition metal cation thereby forming a neutral transition metal compound and a neutral metal by-product. "Compatible anions" are anions which are not degraded to neutrality when the initially formed complex decomposes and are noninterfering with desired subsequent polymerizations. Preferred anions are those containing a single coordination complex comprising a charge-bearing metal or metalloid core carrying a substituent containing an active hydrogen moiety which anion is relatively large (bulky), capable of stabilizing the active catalyst species (the transition metal cation) which is formed when the activator compound and transition metal compound are combined and said anion will be sufficiently labile to be displaced by olefinic, diolefinic and acetylenically unsaturated compounds or other neutral Lewis bases such as ethers, nitriles and the like. Suitable metals for the anions of activator compounds include, but are not limited to, aluminum, gold, platinum and the like. Suitable metalloids include, but are not limited to, boron, phosphorus, silicon and the like. Activator compounds which contain anions comprising a coordination complex containing a single boron atom and a substituent comprising an active hydrogen moiety are preferred.

Preferably, compatible anions containing a substituent comprising an active hydrogen moiety may be represented by the following general Formula (I):

wherein:

M' is a metal or metalloid selected from Groups 5–15 of the Periodic Table of the Elements;

Q independently in each occurrence is selected from the group consisting of hydride, dihydrocarbylamido, preferably dialkylamido, halide, hydrocarbyloxide, preferably alkoxide and aryloxide, hydrocarbyl, and substituted-hydrocarbyl radicals, including halo- substituted hydrocarbyl radicals, and hydrocarbyl- and halohydrocarbyl-substituted organo-metalloid radicals, the hydrocarbyl portion having from 1 to 20 carbons with the proviso that in not more than one occurrence is Q halide;

G is a polyvalent, having r+1 valencies and preferably divalent hydrocarbon radical bonded to M' and T;

T is O, S, NR, or PR, wherein R is a hydrocarbon radicals a trihydrocarbyl silyl radical, a trihydrocarbyl germyl radical, or hydrogen;

m is an integer from 1 to 7, preferably 3;

n is an integer from 0 to 7, preferably 3;

q is an integer 0 or 1, preferably 1;

r is an integer from 1 to 3, preferably 1;

z is an integer from 1 to 8, preferably 1;

d is an integer from 1 to 7, preferably 1; and n+z−m=d.

Preferred boron-containing anions which are particularly useful in this invention may be represented by the following general Formula (II):

wherein:

B is boron in a valence state of 3;

z' is an integer from 1–4, preferably 1;

d is 1; and

Q, G, T, H, q, and r are as defined for Formula (I). Preferably, z' is 1, q is 1, and r is 1.

Illustrative, but not limiting, examples of anions of activator compounds to be used in the present invention are boron-containing anions such as triphenyl(hydroxyphenyl)borate, diphenyl-di(hydroxyphenyl)borate, triphenyl(2,4-dihydroxyphenyl)borate, tri(p-tolyl)(hydroxyphenyl)borate, tris-(pentafluorophenyl)(hydroxyphenyl)borate, tris-(2,4-dimethylphenyl)(hydroxyphenyl)borate, tris-(3,5-dimethylphenyl)(hydroxyphenyl)borate, tris-(3,5-ditrifluoromethylphenyl)(hydroxyphenyl)borate, tris (pentafluorophenyl)(2-hydroxyethyl)borate, tris (pentafluorophenyl)(4-hydroxybutyl)borate, tris (pentafluorophenyl)(4-hydroxycyclohexyl)borate, tris (pentafluorophenyl)(4-(4'-hydroxyphenyl)phenyl)borate, tris(pentafluorophenyl)(6hydroxy-2-naphthyl)borate, and the like. A highly preferred activator complex is tris (pentafluorophenyl)(4-hydroxyphenyl)borate. Other preferred anions of activator compounds are those above mentioned borates wherein the hydroxy functionality is replaced by an amino NHR functionality wherein R preferably is methyl, ethyl, or t-butyl.

The cationic portion b.1) of the activator compound to be used in association with the compatible anion b.2) can be any cation which is capable of reacting with the transition metal compound to form a catalytically active transition metal complex, especially a cationic transition metal complex. The cations b.1) and the anions b.2) are used in such ratios as to give a neutral activator compound. Preferably the cation is selected from the group consisting of Bronsted acidic cations, carbonium cations, silylium cations, and cationic oxidizing agents.

Bronsted acidic cations may be represented by the following general formula:

wherein:

L is a neutral Lewis base, preferably a nitrogen, phosphorus, or sulfur containing Lewis base; and (L—H)⁺ is a Bronsted acid. The Bronsted acidic cations are believed to react with the transition metal compound by transfer of a proton of said cation, which proton combines with one of the ligands on the transition metal compound to release a neutral compound.

Illustrative, but not limiting, examples of Bronsted acidic cations of activator compounds to be used in the present invention are trialkyl-substituted ammonium cations such as triethylammonium, tripropylammonium, tri(n-butyl) ammonium, trimethylammonium, tributylammonium, and tri(n-octyl)ammonium. Also suitable are N,N-dialkyl anilinium cations such as N,N-dimethylanilinium, N,N-diethylanilinium, N,N-2,4,6-pentamethylanilinium, N,N-dimethylbenzylammonium and the like; dialkylammonium cations such as di-(i-propyl)ammonium, dicyclohexylammonium and the like; and triarylphosphonium cations such as triphenylphosphonium, tri(methylphenyl)phosphonium, tri(dimethylphenyl)phosphonium, dimethylsulphonium, diethylsulphonium, and diphenylsulphonium.

A second type of suitable cations corresponds to the formula: $\copyright^+$, wherein $\copyright^+$ is a stable carbonium or silylium ion containing up to 30 nonhydrogen atoms, the cation being capable of reacting with a substituent of the transition metal compound and converting it into a catalytically active transition metal complex, especially a cationic transition metal complex. Suitable examples of cations include tropyllium, triphenylmethylium, benzene(diazonium). Silylium salts have been previously generically disclosed in J. Chem. Soc. Chem. Comm., 1993, 383–384, as well as Lambert, J. B., et. al., Organometallics, 1994, 13, 2430–2443. Preferred silylium cations are triethylsilylium, and trimethylsilylium and ether substituted adducts thereof.

Another suitable type of cation comprises a cationic oxidizing agent represented by the formula:

$$Ox^{e+}$$

wherein $Ox^{e+}$ is a cationic oxidizing agent having a charge of e+, and e is an integer from 1 to 3.

Examples of cationic oxidizing agents include: ferrocenium, hydrocarbyl-substituted ferrocenium, $Ag^+$, and $Pb^{2+}$.

The quantity of activator compound in the supported catalyst component and the supported catalyst is not critical, but typically ranges from 0.1, preferably from 1 to 2,000 micromoles of activator compound per gram of treated support material. Preferably, the supported catalyst or component contains from 10 to 1,000 micromoles of activator compound per gram of treated support material.

The supported catalyst component of the present invention as such or slurried in a diluent can be stored or shipped under inert conditions, or can be used to generate the supported catalyst of the present invention.

Suitable transition metal compounds for use in the supported catalyst of the present invention are those that contain a substituent capable to react with activator compound (b) to thereby form a catalytically active transition metal complex. The transition metal compounds may be derivatives of any transition metal including Lanthanides, preferably from Groups 3, 4, 5, and 6, more preferably of the Group 3 or 4 transition metals or the Lanthanides, which transition metals are in the +2, +3, or +4 formal oxidation state. The transition metals preferably contain at least one π-bonded anionic ligand group which can be a cyclic or noncyclic delocalized π-bonded anionic ligand group. Exemplary of such π-bonded anionic ligand group are conjugated or non-conjugated, cyclic or non-cyclic dienyl groups, allyl groups, aryl groups, as well as substituted derivatives of such groups.

By the term "derivative" when used to describe the above-substituted, delocalized π-bonded groups is meant that each atom in the delocalized π-bonded group may independently be substituted with a radical selected from the group consisting of halogen, hydrocarbyl, halohydrocarbyl, and hydrocarbyl-substituted metalloid radicals wherein the metalloid is selected from Group 14 of the Periodic Table of the Elements. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system or a hydrogenated fused ring system. Suitable hydrocarbyl-substituted organo-metalloid radicals include mono-, di- and tri-substituted organo-metalloid radicals of Group 14 elements wherein each of the hydrocarbyl groups contains from 1 to 20 carbon atoms. More particularly, suitable hydrocarbyl-substituted organo-metalloid radicals include trimethylsilyl, triethylsilyl, ethyldimethylsilyl, methyldiethylsilyl, triphenylgermyl, trimethylgermyl and the like.

Preferred anionic, delocalized π-bonded groups include cyclopentadienyl and substituted cyclopentadienyl groups. Especially preferred are cyclopentadienyl, indenyl, fluorenyl, tetrahydroindenyl, tetrahydrofluorenyl, and octahydrofluorenyl. Other examples of preferred anionic ligand groups are pentadienyl, cyclohexadienyl, dihydroanthracenyl, hexahydroanthracenyl, and decahydroanthracenyl groups, and methyl-substituted derivatives thereof.

Suitable transition metal compounds (c) may be a cyclopentadienyl or substituted cyclopentadienyl derivative of any transition metal including Lanthanides, but preferably of the Group 3, 4, or Lanthanide transition metals. Suitable transition metal compounds for use in the present invention are the bridged or unbridged mono-, bis-, and tri-cyclopentadienyl or substituted cyclopentadienyl transition metal compounds.

Suitable unbridged monocyclopentadienyl or mono (substituted cyclopentadienyl) transition metal derivatives are represented by general Formula (3):

$$CpMX_n \qquad (3)$$

wherein Cp is cyclopentadienyl or a derivative thereof, M is a Group 3, 4, or 5 transition metal having a formal oxidation state of +2, +3 or +4, X independently in each occurrence represents an anionic ligand group (other than a cyclic, aromatic π-bonded anionic ligand group) selected from the group of hydrocarbyl, hydrocarbylene (including hydrocarbadienyl), hydrocarbyloxy, hydride, halo, silyl, germyl, amide, and siloxy radicals having up to 50 nonhydrogen atoms, with the proviso that at least one X is selected from the group of a hydride radical, hydrocarbyl radical, substituted-hydrocarbyl radical, or organo-metalloid radical, and n, a number equal to one less than the formal oxidation state of M, is 1, 2 or 3, preferably 3. Preferably, at least one of X is a hydrocarbyl radical having from 1 to about 20 carbon atoms, a substituted-hydrocarbyl radical having from 1 to about 20 carbon atoms wherein one or more of the hydrogen atoms are replaced with a halogen atom, or an organo-metalloid radical comprising a Group 14 element wherein each of the hydrocarbyl substituents contained in the organo portion of said organo-metalloid, independently, contain from 1 to about 20 carbon atoms.

Suitable bridged monocyclopentadienyl or mono (substituted cyclopentadienyl) transition metal compounds include the so-called constrained geometry complexes.

Examples of such complexes and methods for their preparation are disclosed in U.S. application Ser. No. 545,403, filed Jul. 3, 1990 (corresponding to EP-A-416,815), U.S. application Ser. No. 241,523, filed May 12, 1994, now U.S. Pat. No. 5,470,993 (corresponding to WO-95/00526), as well as U.S. Pat. Nos. 5,055,438, 5,057,475, 5,096,867, 5,064,802 5,132,380, and 5,374,696 all of which are incorporated herein by reference.

More particularly, preferred bridged monocyclopentadienyl or mono(substituted cyclopentadienyl) transition metal compounds correspond to the Formula (IV):

wherein:

M is a metal of Group 3–5, especially a Group 4 metal, particularly titanium;

Cp* is a substituted cyclopentadienyl group bound to Z' and, in an $\eta^5$ bonding mode, to M or such a group is further substituted with from one to four substituents selected from the group consisting of hydrocarbyl, silyl, germyl, halo, hydrocarbyloxy, amine, and mixtures thereof, said substituent having up to 20 nonhydrogen atoms, or optionally, two such further substituents together cause Cp* to have a fused ring structure;

Z' is a divalent moiety other than a cyclic or noncyclic π-bonded anionic ligand, said Z' comprising boron, or a member of Group 14 of the Periodic Table of the Elements, and optionally nitrogen, phosphorus, sulfur or oxygen, said moiety having up to 20 non-hydrogen atoms, and optionally Cp* and Z' together form a fused ring system;

X has the same meaning as in Formula (III); and n is 1 or 2 depending on the valence of M.

In consonance with the previous explanation, M is preferably a Group 4 metal, especially titanium; n is 1 or 2; and X is monovalent ligand group of up to 30 nonhydrogen atoms, more preferably, $C_{1-20}$ hydrocarbyl.

When n is 1 and the Group 3–5 metal (preferably the Group 4 metal) is in the +3 formal oxidation state, X is preferably a stabilizing ligand.

By the term "stabilizing ligand" is meant that the ligand group stabilizes the metal complex through either:

1) a nitrogen, phosphorus, oxygen or sulfur chelating bond, or 2) an η3 bond with a resonant, delocalized π-electronic structure.

Examples of stabilizing ligands of group 1) include silyl, hydrocarbyl, amido or phosphido ligands substituted with one or more aliphatic or aromatic ether, thioether, amine or phosphine functional groups, especially such amine or phosphine groups that are tertiary-substituted, said stabilizing ligand having from 3 to 30 nonhydrogen atoms. Most preferred group 1) stabilizing ligands are 2-dialkylaminobenzyl or 2-(dialkylaminomethyl)phenyl groups containing from 1 to 4 carbons in the alkyl groups.

Examples of stabilizing ligands of group 2) include $C_{3-10}$ hydrocarbyl groups containing ethylenic unsaturation, such as allyl, 1-methylallyl, 2-methylallyl, 1,1-dimethylallyl, or 1,2,3-trimethylallyl groups.

More preferably still, such metal coordination complexes correspond to the Formula (V):

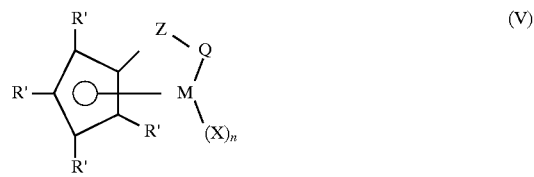

wherein R' in each occurrence is independently selected from the group consisting of hydrogen, hydrocarbyl, silyl, germyl, cyano, halo and combinations thereof having up to 20 nonhydrogen atoms, or two R' groups together form a divalent derivative thereof;

X has the same meaning as defined for Formula (III);

Q is a divalent anionic ligand group comprising nitrogen, phosphorus, oxygen or sulfur and having up to 20 non-hydrogen atoms, said Q being bonded to Z and M through said nitrogen, phosphorus, oxygen or sulfur, and optionally Q and Z together form a fused ring system;

M is a Group 4 metal, especially titanium;

Z is $SiR^*_2$, $CR^*_2$, $SiR^*_2SiR^*_2$, $CR^*_2CR^*_2$, $CR^*=CR^*$, $CR^*_2SiR^*_2$, $GeR^*2$, $BR^*$, or $BR^*2$; wherein:

R* in each occurrence is independently selected from the group consisting of hydrogen, hydrocarbyl, silyl, halogenated alkyl, halogenated aryl groups having up to 20 non-hydrogen atoms, and mixtures thereof, or two or more R* groups from Z, or an R* group from Z together with Y form a fused ring system; and n is 1 or 2.

Further more preferably, Q is —O—, —S—, —NR*—, —PR*—. Highly preferably Q is a nitrogen or phosphorus containing group corresponding to the formula —N(R')— or —P(R')—, wherein R' is as previously described, ie., an amido or phosphido group.

Most highly preferred metal coordination complexes correspond to the Formula (VI):

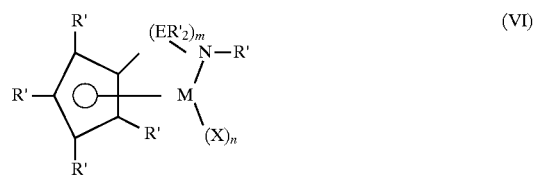

wherein:

M is titanium;

R' each occurrence is independently selected from the group consisting of hydrogen, silyl, hydrocarbyl and combinations thereof having up to 10 carbon or silicon atoms, or two R' groups of the substituted cyclopentadienyl moiety are joined together;

E is silicon or carbon;

X independently each occurrence is hydride, alkyl, aryl, of up to 10 carbons;

m is 1 or 2; and n is 1 or 2.

Examples of the above most highly preferred metal coordination compounds include compounds wherein the R' on the amido group is methyl, ethyl, propyl, butyl, pentyl, hexyl, (including isomers), norbornyl, benzyl, phenyl, and cyclododecyl; $(ER'_2)_m$ is dimethyl silane or 1,2-ethylene; R' on the cyclic π-bonded group independently each occurrence is hydrogen, methyl, ethyl, propyl, butyl, pentyl, hexyl, norbornyl, benzyl, and phenyl, or two R' groups are joined forming an indenyl, tetrahydroindenyl, fluorenyl or octahydrofluorenyl moiety; and X is methyl, ethyl, propyl, butyl, pentyl, hexyl, norbornyl, benzyl, and phenyl.

Transition metal compounds wherein the transition metal is in the +2 formal oxidation state include those complexes containing one and only one cyclic, delocalized, anionic, π-bonded group, said complexes corresponding to the Formula (VII):

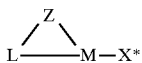
(VII)

wherein:

M is titanium or zirconium in the +2 formal oxidation state;

L is a group containing a cyclic, delocalized, anionic, π-system through which the group is bonded to M, and which group is also bonded to Z;

Z is a moiety bonded to M via a σ-bond, comprising boron, or a member of Group 14 of the Periodic Table of the Elements, and also comprising nitrogen, phosphorus, sulfur or oxygen, said moiety having up to 60 non-hydrogen atoms; and X* is a neutral, conjugated or nonconjugated diene, optionally substituted with one or more hydrocarbyl groups, said X having up to 40 carbon atoms and forming a π-complex with M.

Preferred transition metal compounds of Formula (VII) include those wherein Z, M and X* are as previously defined; and L is a $C_5H_4$ group bonded to Z and bound in an $\eta^5$ bonding mode to M or is such an $\eta^5$ bound group substituted with from one to four substituents independently selected from hydrocarbyl, silyl, germyl, halo, cyano, and combinations thereof, said substituent having up to 20 nonhydrogen atoms, and optionally, two such substituents (except cyano or halo) together cause a fused ring structure.

More preferred transition metal +2 compounds according to the present invention correspond to the Formula (VIII):

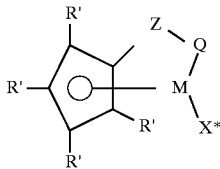
(8)

wherein:

R' in each occurrence is independently selected from hydrogen, hydrocarbyl, silyl, germyl, halo, cyano, and combinations thereof, said R' having up to 20 nonhydrogen atoms, and optionally, two R' groups (where R' is not hydrogen, halo or cyano) together form a divalent derivative thereof connected to adjacent positions of the cyclopentadienyl ring to form a fused ring structure;

X* is a neutral $\eta^4$-bonded diene group having up to 30 nonhydrogen atoms, which forms a π-complex with M;

Q is —O—, —S—, —NR*—, —PR*—;

M is titanium or zirconium in the +2 formal oxidation state;

Z* is $SiR^*_2$, $CR^*_2$, $SiR^*_2SiR^*_2$, $CR^*2CR^*2$, $CR^*=CR^*$, $CR^*_2SiR^*_2$, or $GeR^*_2$; wherein:

R* each occurrence is independently hydrogen, or a member selected from hydrocarbyl, silyl, halogenated alkyl, halogenated aryl, and combinations thereof, said R* having up to 10 nonhydrogen atoms, and optionally, two R* groups from Z* (when R* is not hydrogen), or an R* group from Z* and an R* group from Y form a ring system.

Preferably, R' independently each occurrence is hydrogen, hydrocarbyl, silyl, halo and combinations thereof said R' having up to 10 nonhydrogen atoms, or two R' groups (when R' is not hydrogen or halo) together form a divalent derivative thereof; most preferably, R' is hydrogen, methyl, ethyl, propyl, butyl, pentyl, hexyl, (including where appropriate all isomers), cyclopentyl, cyclohexyl, norbornyl, benzyl, or phenyl or two R' groups (except hydrogen) are linked together, the entire $C_5R'_4$ group thereby being, for example, an indenyl, tetrahydroindenyl, fluorenyl, tetrahydrofluorenyl, or octahydrofluorenyl group.

Further preferably, at least one of R' or R* is an electron donating moiety. By the term "electron donating" is meant that the moiety is more electron donating than hydrogen. Thus, highly preferably Y is a nitrogen or phosphorus containing group corresponding to the formula —N(R")— or —P(R")—, wherein R" is $C_{1-10}$ a hydrocarbyl.

Examples of suitable X* groups include: s-trans-$\eta^4$-1,4-diphenyl-1,3-butadiene; s-trans-$\eta^4$-3-methyl-1,3-pentadiene; s-trans-$\eta^4$-1,4-dibenzyl-1,3-butadiene; s-trans-$\eta^4$-2,4-hexadiene; s-trans-$\eta^4$-1,3-pentadiene; s-trans-$\eta^4$-1,4-ditolyl-1,3-butadiene; s-trans-$\eta^4$-1,4-bis(trimethylsilyl)-1,3-butadiene; s-cis-$\eta^4$-1,4-diphenyl-1,3-butadiene; s-cis-$\eta^4$-3-methyl-1,3-pentadiene; s-cis-$\eta^4$-1,4-dibenzyl-1,3-butadiene; s-cis-$\eta^4$-2,4-hexadiene; s-cis-$\eta^4$-1,3-pentadiene; s-cis-$\eta^4$-1,4-ditolyl-1,3-butadiene; and s-cis-$\eta^4$-1,4-bis(trimethylsilyl)-1,3-butadiene, said s-cis diene group forming a π-complex as defined herein with the metal.

Most highly preferred transition metal +2 compounds are amidosilane- or amidoalkanediyl- compounds of Formula VIII) wherein:

—Z*—Y—is —$(ER'''_2)_m$—N(R")—, and R' each occurrence is independently selected from hydrogen, silyl, hydrocarbyl and combinations thereof, said R' having up to 10 carbon or silicon atoms, or two such R' groups on the substituted cyclopentadienyl group (when R' is not hydrogen) together form a divalent derivative thereof connected to adjacent positions of the cyclopentadienyl ring;

R" is $C_{1-10}$ hydrocarbyl;

R''' is independently each occurrence hydrogen or $C_{1-10}$ hydrocarbyl;

E is independently each occurrence silicon or carbon; and m is 1 or 2.

Examples of the metal complexes according to the present invention include compounds wherein R" is methyl, ethyl, propyl, butyl, pentyl, hexyl, (including all isomers of the foregoing where applicable), cyclododecyl, norbornyl, benzyl, or phenyl; $(ER'''_2)_m$ is dimethylsilane, or ethanediyl; and the cyclic delocalized π-bonded group is cyclopentadienyl, tetramethylcyclopentadienyl, indenyl, tetrahydroindenyl, fluorenyl, tetrahydrofluorenyl or octahydrofluorenyl.

Suitable bis(cyclopentadienyl) derivatives of transition metals include those of titanium, zirconium and hafnium compounds and may be represented by the following general Formulae (IX)–(XII):

  (IX)

  (X)

  (XI)

-continued

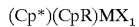 (XII)

wherein: M is a Group 4 metal namely titanium (Ti), zirconium (Zr) and hafnium (Hf); (A—Cp) is either (Cp) (Cp*) or Cp—A'—Cp* and Cp and Cp* are the same or different cyclopentadienyl radicals, as well as substituted derivatives of cyclopentadienyl radicals, and A' is a covalent bridging group containing a Group 14 element; L is an olefin, diolefin or aryne ligand; at least one of $X_1$ and $X_2$ is a hydride radical, hydrocarbyl radical, substituted-hydrocarbyl radical, or organo-metalloid radical, the other of $X_1$ and $X_2$ being a hydride radical, hydrocarbyl radical, substituted-hydrocarbyl radical, organo-metalloid radical, or a hydrocarbyloxy radical; preferably one or both of $X_1$ and $X_2$ is a hydrocarbyl radical having from 1 to about 20 carbon atoms, substituted-hydrocarbyl radical having from 1 to about 20 carbon atoms wherein one or more of the hydrogen atoms are replaced with a halogen atom, organo-metalloid radical comprising a Group 14 element wherein each of the hydrocarbyl substituents contained in the organo portion of said organo-metalloid, independently, contain from 1 to about 20 carbon atoms; $X'_1$ and $X'_2$ are joined and bound to the metal atom to form a metallacycle, in which the metal, $X'_1$ and $X'_2$ form a hydrocarbocyclic ring containing from about 3 to about 20 carbon atoms; and R is a substituent, preferably a hydrocarbyl substituent, having from 1 to 20 carbon atoms on one of the cyclopentadienyl radicals, which is also bound to the metal atom.

When not both $X_1$ and $X_2$ are a hydride radical, hydrocarbyl radical, substituted-hydrocarbyl radical, or organo-metalloid radical one of these can be a hydrocarbyloxy radical having from 1 to 20 carbon atoms. Suitable examples of hydrocarbyloxy radicals include alkyloxy, aryloxy, aralkyloxy, and alkaryloxy radicals having from 1 to 20 carbon atoms, more preferably alkyl radicals having from 1 to 6 carbon atoms, and aryl, aralkyl and alkaryl radicals having from 6 to 10 carbon atoms, even more preferably isopropyloxy, n-butyloxy, or t-butyloxy.

Examples of such bis(cyclopentadienyl) derivatives of transition metals and methods for their preparation are disclosed in U.S. Pat. No. 5,384,299 (corresponding to EP-A-277,004) and U.S. application Ser. No. 459,921, filed Jan. 2, 1990 (corresponding to WO-91/09882), which are incorporated herein by reference.

Suitable tri-cyclopentadienyl or substituted cyclopentadienyl transition metal compounds include those containing a bridging group linking two cyclopentadienyl groups and those without such bridging groups.

Suitable unbridged tri-cyclopentadienyl transition metal derivatives are represented by general Formula (XIII):

 (XIII)

wherein Cp, M and X are as defined for Formula (III) and n" is three less than the formal oxidation state of M and is 0 or 1, preferably 1. Preferred ligand groups X are hydrocarbyl, hydrocarbyloxy, hydride, halo, silyl, germyl, amide, and siloxy.

Generally, the ratio of moles of activator compound (b) to gramatoms of transition metal in compound (c) in the supported catalyst is from 0.05:1 to 100:1, preferably from 0.5:1 to 20:1 and most preferably from 1:1 to 5:1 mole activator compound per gramatom of transition metal in the transition metal compound. At too low ratios the supported catalyst will not be very active, whereas at too high ratios the catalyst becomes less economic due to the relatively high cost associated with the use of large quantities of activator compound.

The supported catalyst component of the present invention can be prepared by combining the support material with the organometal compound, preferably an aluminum component, and the activator compound. The order of addition is not critical. The organometal compound may be either first combined with the support material or with the activator compound, and subsequently the activator compound or the support material may be added. One preferred embodiment comprises treating the support material first with the organometal compound, preferably aluminum component by combining the organometal compound in a suitable solvent, such as a hydrocarbon solvent, with the support material. The temperature, pressure, and contact time for this treatment are not critical, but generally vary from −20° C. to about 150° C., from subatmospheric to 10 bar, more preferably at atmospheric pressure, for 5 minutes to 48 hours. Usually the slurry is agitated. After this treatment the solids are typically separated from the solvent. Any excess of organometal compound could then be removed by techniques known in the art. This method is especially suitable for obtaining support material with relatively low metal, preferably aluminum, loadings.

According to a preferred embodiment, the support material is first subjected to a thermal treatment at 100° C. to 1000° C., preferably at about 200° C. to about 850° C. Typically, this treatment is carried out for about 10 minutes to about 72 hours, preferably from about 0.5 hours to 24 hours. Then the thermally treated support material is combined with the organometal compound, preferably $AlR'_3$ wherein R' has the meaning defined hereinbefore in a suitable diluent or solvent, preferably one in which the organometal compound is soluble. Typical solvents are hydrocarbon solvents having from 5 to 12 carbon atoms, preferably aromatic solvents such as toluene and xylenes, or aliphatic solvents of 6 to 10 carbon atoms, such as hexane, heptane, octane, nonane, decane, and isomers thereof, cycloaliphatic solvents of 6 to 12 carbon atoms such as cyclohexane, or mixtures of any of these.

The support material is combined with the organometal compound at a temperature of −20° C. to 150° C., preferably at 20° C. to 100° C. The contact time is not critical and can vary from 5 minutes to 72 hours, and is preferably from 0.5 hours to 36 hours. Agitation is preferably applied. The thus treated support material is then preferably contacted with the activator compound.

An alternative treatment of the support material, suitable for obtaining alumoxane loadings attached to the support material, involves one or both of the following steps A and B:

A. heating a support material containing alumoxane under an inert atmosphere for a period and at a temperature sufficient to fix alumoxane to the support material;

B. subjecting the support material containing alumoxane to one or more wash steps to remove alumoxane not fixed to the support material;

thereby selecting the conditions in heating step A and washing step B so as to form a treated support material wherein not more than about 10 percent aluminum present in the treated support material cis extractable in a one hour extraction with toluene of 90° C. using about 10 mL toluene per gram of supported catalyst component. High amounts of alumoxane attached to the support material are obtained using first heating step A., optionally followed by wash step B.

In this process the alumoxane treated support material may be obtained by combining in a diluent an alumoxane with a support material containing from zero to not more than 20 weight percent of water, preferably from zero to not more than 6 weight percent of water, based on the total weight of support material and water. Although support materials containing substantially no water give good results with respect to catalytic properties of the supported catalyst, it has been found that support materials containing relatively small amounts of water can be used without problem in the present process. The water containing support materials when combined under identical conditions with the same amount of alumoxane gives in the present process a supported catalyst component having a slightly higher aluminum content than the substantially water-free support material. It is believed that the water reacts with the residual amounts of aluminum alkyl present in the alumoxane to convert the aluminum alkyl to extra alumoxane. An additional advantage is that in this way less aluminum alkyl will be lost to waste or recycle streams. The alumoxane desirably is used in a dissolved form.

Alternatively, the alumoxane pretreated support material may be obtained by combining in a diluent, a support material containing from 0.5 to 50 weight percent water, preferably from 1 to 20 weight percent water, based on the total weight of support material and water, with a compound of the formula $R''_{n^*}AlX''_{3-n^*}$ wherein R" in independently each occurrence is a hydrocarbyl radical, X" is halogen or hydrocarbyloxy, and n* is an integer from 1 to 3. Preferably, n* is 3. R" in independently each occurrence is preferably an alkyl radical, advantageously one containing from 1 to 12 carbon atoms. Preferred alkyl radicals are methyl, ethyl, propyl, isopropyl, n-butyl, isobutyl, tert-butyl, pentyl, isopentyl, hexyl, iso-hexyl, heptyl, octyl, and cyclohexyl. Highly preferred compounds of formula $R''_{n}*AlX''_{3-n^*}$ are trimethylaluminum, triethylaluminum and tri-isobutylaluminum. When the alumoxane is prepared in situ by reacting the compound of the formula $R''_{n^*}AlX''_{3-n^*}$ with water, the mole ratio of $R''_{n^*}AlX''_{3-n^*}$ to water is typically 10:1 to 1:1, preferably from 5:1 to 1:1.

The support material is added to the alumoxane or compound of the formula $R''_{n^*}AlX''_{3-n^*}$, preferably dissolved in a solvent, most preferably a hydrocarbon solvent, or the solution of alumoxane or compound of the formula $R''_{n^*}AlX''_{3-n^*}$ is added to the support material. The support material can be used as such in dry form or slurried in a hydrocarbon diluent. Both aliphatic and aromatic hydrocarbons can be used. Suitable aliphatic hydrocarbons include, for example, pentane, isopentane, hexane, heptane, octane, iso-octane, nonane, isononane, decane, cyclohexane, methylcyclohexane and combinations of two or more of such diluents. Suitable examples of aromatic diluents are benzene, toluene, xylene, and other alkyl or halogen-substituted aromatic compounds. Most preferably, the diluent is an aromatic hydrocarbon, especially toluene. Suitable concentrations of solid support in the hydrocarbon medium range from about 0.1 to about 15, preferably from about 0.5 to about 10, more preferably from about 1 to about 7 weight percent. The contact time and temperature are not critical. Preferably the temperature is from 0° C. to 60° C., more preferably from 10° C. to 40° C. The contact time is from 15 minutes to 40 hours, preferably from 1 to 20 hours.

Before subjecting the alumoxane-treated support material to the heating step or washing step, the diluent or solvent is preferably removed to obtain a free flowing powder. This is preferably done by applying a technique which only removes the liquid and leaves the aluminum compounds on the solids, such as by applying heat, reduced pressure, evaporation, or a combination thereof. If desired, the removal of diluent can be combined with the heating step, although care should be taken that the diluent is removed gradually.

The heating step and/or the washing step are conducted in such a way that a very large proportion (more than about 90 percent by weight) of the alumoxane which remains on the support material is fixed. Preferably, a heating step is used, more preferably a heating step is used followed by a washing step. When used in the preferred combination both steps cooperate such that in the heating step the alumoxane is fixed to the support material, whereas in the washing step the alumoxane which is not fixed is removed to a substantial degree. The upper temperature for the heat-treatment is preferably below the temperature at which the support material begins to agglomerate and form lumps which are difficult to redisperse, and below the alumoxane decomposition temperature. When the transition metal compound c) is added before the heat treatment, the heating temperature should be below the decomposition temperature of the transition metal compound. Preferably, the heat-treatment is carried out at a temperature from 75° C. to 250° C. for a period from 15 minutes to 24 hours. More preferably, the heat treatment is carried out at a temperature from 160° C. to 200° C. for a period from 30 minutes to 4 hours. Good results have been obtained while heating for 8 hours at 100° C. as well as while heating for 2 hours at 175° C. By means of preliminary experiments, a person skilled in the art will be able to define the heat-treatment conditions that will provide the desired result. It is also noted, that the longer the heat treatment takes, the higher the amount of alumoxane fixed to the support material will be. The heat-treatment is carried out at reduced pressure or under an inert atmosphere, such as nitrogen gas, or both but preferably at reduced pressure. Depending on the conditions in the heating step, the alumoxane may be fixed to the support material to such a high degree that a wash step may be omitted.

In the wash step, the number of washes and the solvent used are such that sufficient amounts of nonfixed alumoxane are removed. The washing conditions should be such that non-fixed alumoxane is soluble in the wash solvent. The support material containing alumoxane, preferably already subjected to a heat-treatment, is preferably subjected to one to five wash steps using an aromatic hydrocarbon solvent at a temperature from 0° C. to 110° C. More preferably, the temperature is from 20° C. to 100° C. Preferred examples of aromatic solvents include toluene, benzene and xylenes. More preferably, the aromatic hydrocarbon solvent is toluene. At the end of the wash treatment, the solvent is removed by a technique that also removes the alumoxane dissolved in the solvent, such as by filtration or decantation. Preferably, the wash solvent is removed to provide a free flowing powder.

The organometal compound treated support material is then typically reslurried in a suitable diluent and combined with the activator compound. The activator compound is preferably used in a diluent. Suitable diluents include hydrocarbon and halogenated hydrocarbon diluents. Any type of solvent or diluent can be used which does not react with the catalyst components in such a way as to negatively impact the catalytic properties. Preferred diluents are aromatic hydrocarbons, such as toluene, benzene, and xylenes, and aliphatic hydrocarbons such as hexane, heptane, and cyclohexane. Preferred halogenated hydrocarbons include methylene chloride and carbon tetrachloride. The temperature is not critical but generally varies between −20° C. and the decomposition temperature of the activator. Typical contact times vary from a few minutes to several days. Agitation of the reaction mixture is preferred. Advantageously, the activator compound is dissolved, using heat to assist in dissolution where desired. It may be desirable to carry out the contacting between the organometal-treated support material and the activator compound at elevated temperatures. Preferably, such elevated temperatures are from 45° C. to 120° C.

Instead of first treating the support material with the organometal compound, preferably aluminum component, and subsequently adding the activator compound, the organometal compound, preferably aluminum component, and activator compound may be combined in a suitable diluent prior to adding or combining the reaction mixture to or with the support material.

Without wishing to be bound by any theory, it is believed that an organo group of the organometal compound reacts with the active hydrogen moiety contained in the activator anion b.2) to form a reaction product (hereinafter also referred to as "adduct"). For example, when the organometal compound is trialkylaluminum AlR$_3$ and the active hydrogen-containing moiety is represented by G—OH, the reaction product is believed to comprise G—O—AlR$_2$ whereas further an alkane by-product RH is formed. This adduct G—O—AlR$_2$ when combined with the support material containing hydroxyl groups, Si—OH in case of a silica support material, is believed to form Si—O—Al(R)—O—G together with alkane RH as by-product. This method of preparing the supported catalyst component has been found to run very smoothly and to provide catalysts and catalyst precursors or components having desirable properties. Typical ratios to be used in this reaction are from about 1:1 to about 20:1 moles of organometal compound to mole equivalents of active hydrogen moieties contained in the activator anion b.2).

The amount of adduct, formed by combining the organometal compound with the activator compound, to be combined with the support material is not critical. Preferably, the amount is not higher than can be fixed to the support material. Typically, this is determined by the amount of support material hydroxyls. The amount of adduct to be employed is preferably not more than the equivalent amount of such hydroxyl groups. Less than the equivalent amount is preferably used, more preferably the ratio between moles of adduct to moles of surface reactive groups such as hydroxyls is between 0.01 and 1, even more preferably between 0.02 and 0.8. Prior to adding the transition metal compound it is preferred, especially when less than an equivalent amount of adduct is added with respect to surface reactive groups, to add an additional amount of organometal compound to the reaction product of support material and the adduct to remove any remaining surface reactive groups which otherwise may react with the transition metal and thus require higher amounts thereof to achieve equal catalytic activity. Prior to combining it with the transition metal compound, the supported catalyst component can be washed, if desired, to remove any excess of adduct or organometal compound.

The supported catalyst component comprising the support material, organometal compound, and the activator may be isolated to obtain a free flowing powder by removing the liquid medium using preferably filtration or evaporation techniques.

Although the transition metal compound may be combined with the activator compound, or the adduct of the organometal compound and the activator compound, prior to combining the activator compound or its adduct with the support material, this results in reduced catalyst efficiencies. Preferably, the transition metal is first combined with the support material treated with the organometal component and before adding the activator compound, or the transition metal is added after the treated support material and activator have been combined, or after the activator adduct and the support material have been combined. Most preferably, the transition metal compound (c) is added to the reaction product of the support material treated with the organometal compound and activator compound, or after the activator adduct and the support material have been combined.

The transition metal compound is preferably used dissolved in a suitable solvent, such as a hydrocarbon solvents advantageously a $C_{5-10}$ aliphatic or cycloaliphatic hydrocarbon or a $C_{6-10}$ aromatic hydrocarbon. The contact temperature is not critical provided it is below the decomposition temperature of the transition metal and of the activator. Good results are obtained in a temperature range of 0° C. to 100° C. All steps in the present process should be conducted in the absence of oxygen and moisture.

Upon combining the transition metal compound with the supported catalyst component, the supernatant liquid typically is colorless indicating that the transition metal compound, which solution typically is colored, substantially remains with the solid supported catalyst.

The supported catalyst obtained by combining the support material, the organometal compound, the activator, and the transition metal may be stored or shipped in free flowing form under inert conditions after removal of the solvent.

The supported catalysts of the present invention may be used in an addition polymerization process wherein one or more addition polymerizable monomers are contacted with the supported catalyst of the invention under addition polymerization conditions.

Suitable addition polymerizable monomers include ethylenically unsaturated monomers, acetylenic compounds, conjugated or non-conjugated dienes, polyenes, and carbon monoxide. Preferred monomers include olefins, for examples alpha-olefins having from 2 to about 20, preferably from about 2 to about 12, more preferably from about 2 to about 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof. Preferably, the alpha-olefins are ethylene, propene, 1-butene, 4-methyl-pentene-1, 1-pentene, 1-hexene, 1-octene, and combinations of ethylene and/or propene with one or more of such other alpha-olefins. Suitable dienes include those having from 4 to 30 carbon atoms, especially those having 5 to 18 carbon atoms. Typical of these are α,ω-dienes, α-internal dienes, including those dienes which are typically used for preparing EPDM type elastomers. Typical examples include 1,3-butadiene, 1,3- and 1,4-pentadiene, 1,3-, 1,4-, and 1,5-hexadiene, 1,7-octadiene, 1,9-decadiene, and lower alkyl substituted analogues of any of these. Other preferred monomers include styrene, halo- or alkyl substituted styrenes, tetrafluoroethylene, vinylcyclobutene, dicyclopentadiene, and ethylidene norbornenes. Suitable addition polymerizable monomers include also any mixtures of the above-mentioned monomers.

The supported catalyst can be formed in situ in the polymerization mixture by introducing into said mixture both a supported catalyst component of the present invention, or its components, as well as a suitable transition metal compound (c).

The supported catalyst can be used as such or after being subjected to prepolymerization. The prepolymerization can be carried out by any known methods such as by bringing a small amount of monomers, preferably alpha-olefins, into contact with the supported catalyst.

The catalyst may be used in the polymerization reaction in a concentration of $10^{-9}$ to $10^{-3}$ moles, based on transition metal, per liter diluent or reaction volume, but is preferably used in a concentration of less than $10^{-5}$, preferably from $10^{-8}$ to $9 \times 10^{-6}$ moles per liter diluent or reaction volume.

The supported catalyst can be advantageously employed in a high pressure, solution, slurry or gas phase polymerization process. A high pressure process is usually carried out at temperatures from 100° C. to 400° C. and at pressures above 500 bar. A slurry process typically uses an inert hydrocarbon diluent and temperatures of from about 0° C. up to a temperature just below the temperature at which the resulting polymer becomes substantially soluble in the inert polymerization medium. Preferred temperatures are from about 30° C., preferably from about 60° C. to about 115° C., preferably to about 100° C. The solution process is carried out at temperatures from the temperature at which the resulting polymer is soluble in an inert solvent up to about 275° C. Generally, solubility of the polymer depends on its density. For ethylene copolymers having densities of 0.86 g/cm³, solution polymerization may be achieved at temperatures as low as about 60° C. Preferably, solution polymerization temperatures range from about 75° C., more preferably from about 80° C., and typically from about 130° C. to about 260° C., more preferably to about 170° C. Most preferably, temperatures in a solution process are between about 80° C. and 150° C. As inert solvents typically hydrocarbons and preferably aliphatic hydrocarbons are used. The solution and slurry processes are usually carried out at pressures between about 1 to 100 bar. Typical operating conditions for gas phase polymerizations are from 20° C. to 100° C., more preferably from 40° C. to 80° C. In gas phase processes the pressure is typically from subatmospheric to 100 bar.

Preferably for use in gas phase polymerization processes, the support has a median particle diameter from about 20 to about 200 μm, more preferably from about 30 μm to about 150 μm, and most preferably from about 50 μm to about 100 μm. Preferably for use in slurry polymerization processes, the support has a median particle diameter from about 1 μm to about 200 μm, more preferably from about 5 μm to about 100 μm, and most preferably from about 20 μm to about 80 μm. Preferably for use in solution or high pressure polymerization processes, the support has a median particle diameter from about 1 μm to about 40 μm, more preferably from about 2 μm to about 30 μm, and most preferably from about 3 μm to about 20 μm.

Further details for polymerization conditions in a gas phase polymerization process can be found in U.S. Pat. Nos. 4,588,790, 4,543,399, 5,352,749, 5,405,922, U.S. application Ser. No. 926,009, filed Aug. 5, 1992 (corresponding to WO-94/03509), and U.S. application Ser. No. 122,582, filed Sep. 17, 1993 (corresponding to WO-95/07942), which are incorporated herein by reference. Gas phase processes wherein condensed monomer or inert diluent is present are preferred.

The supported catalysts of the present invention, also when used in a slurry process or gas phase process, not only are able to produce ethylene copolymers of densities typical for high density polyethylene, in the range of 0.970 to 0.940 g/cm³, but surprisingly, also enable the production of copolymers having substantially lower densities. Copolymers of densities lower than 0.940 g/cm³ and especially lower than 0.930 g/cm³ down to 0.880 g/cm³ or lower can be made while retaining good bulk density properties and while preventing or substantially eliminating reactor fouling. The present invention is capable of producing olefin polymers and copolymers having weight average molecular weights of more than 30,000, preferably more than 50,000, most preferably more than 100,000 up to 1,000,000 and even higher. Typical molecular weight distributions $M_w/M_n$ range from 1.5 to 15, or even higher, preferably between 2.0 and 8.0.

In the polymerization process of the present invention impurity scavengers may be used which serve to protect the supported catalyst from catalyst poisons such as water, oxygen, and polar compounds. These scavengers can generally be used in amounts depending on the amounts of impurities. Typical scavengers include organometal compounds, and preferably trialkylaluminum or boron compounds and alumoxanes.

In the present polymerization process also molecular weight control agents can be used, such as hydrogen or other chain transfer agents. The polymers that are prepared according to such polymerization process may be combined with any conventional additives, such as UV stabilizers, antioxidants, anti-slip or antiblocking agents, which may be added in conventional ways, for example, downstream of the polymerization reactor, or in an extrusion or molding step.

Upon or after removal of the polymerization mixture or product of from the polymerization reactor, the supported catalyst may be deactivated by exposure to air or water, or through any other catalyst deactivating agent or procedure.

In the complex compounds of the present invention, preferably the compatible anion portion b.2) corresponds to general Formula (I):

wherein:

M', Q, G, T, m, n, q, r, z, and d have the same definitions as in formula 1, and Bl is hydrogen H or a protecting group. Preferred protecting groups and charge balancing cations are illustrated hereinafter.

The complex compounds containing anions b.2) can be prepared by combining a neutral compound, such as $M'^{m+}Q_m$, wherein M', Q, and m have the same meaning as in Formula (I), with an active metal derivative of the substituent comprising an active hydrogen moiety, such as a lithium or Grignard derivative thereof, for example $Z(Gq(T-H)_r)$, wherein Z is Li+, MgCl+, MgBr+, or MgI+, and G, T, H, q, and r have the same meanings as in Formula (I). The group T—H can be protected during the preparation by methods which are well known by those skilled in the art. For example, a hydroxy moiety may be protected by a trimethylsilyl group. The method for preparing the complex compounds thus comprises combining in a suitable solvent or diluent a compound $M'^{m+}Q_m$ with a compound of the formula $Z^1(G_q(T-Bl)_r)$, wherein $Z^1$ is $[M*X]^+$ or $[M]^+$ and M* is a Group 2 element, M** is a Group 1 element and X is halogen, G, T, Bl, q, and r have the same meaning as given for Formula (I), optionally followed by recovering the product complex.

Suitable examples of protecting groups Pr include: trialkylsilyl, triarylsilyl, and mixtures thereof, preferably trimethylsilyl, t-butyldimethylsilyl, tri-isopropyl silyl, t-butyldiphenyl silyl, and phenyldimethylsilyl; preferably the protective group contains a bulky substituent, such as t-butyl or phenyl, to stabilize the resulting protected group during the subsequent metalation reaction.

The reaction between the compound $M'^{m+}Q_m$ and $Z^1(Gq(T-Bl)_r)$ is typically carried out in an ether or any other organic diluent that does not negatively impact the desired reaction, and mixtures thereof. Preferred ethers are tetrahydrofuran and diethylether. The temperature is not critical and is typically in the range of −20° C. to 100° C. The reaction mixture is preferably stirred and reacted for a period of between 5 minutes and 72 hours.

It has been found advantageous to use a molar excess of the compound $Z^1(G_q(T—Bl)_r)$ with respect to the compound $M^{'m+}Q_m$. Such excess is preferably 1.1 to 3 mole equivalents, more preferably 1.5 to 2.5 mole equivalents of $Z^1(G_q(T—Bl)_r)$ per mole of $M^{'m+}Q_m$. Preferably, the reaction mixture is heated to a temperature between 40° C. and 100° C., more preferably between 50° C. and 95° C. Using such process conditions were found to increase the conversion based on the compound $M^{'m+}Q_m$ up to 90% and higher. As the compound $M^{'m+}Q_m$ is usually the more expensive reactant, it is highly desirable to increase the yield of the reaction with respect to this compound.

The product complex is then preferably recovered, for example by decantation, filtration, advantageously followed by washing, preferably with a hydrocarbon, and drying.

The protective group Pr when present in the product complex is preferably removed by conventional methods, such as reacting the product complex with water, alcohol, organic acids like acetic acid, organic anhydride compounds such as acetic anhydride containing iron trichloride, and tetra-hydrocarbyl ammonium fluorides, such as $Bu_4NF$. It has been found advantageous to use the hydrogen fluoride adduct of a tertiary amine. This adduct is capable of removing protecting groups, also those containing bulky ligands, such as t-butyl or phenyl, and thereby give a by-product ammonium cation which is a cation that can react with the transition metal compound to give a catalytically active complex. Using this adduct is preferred over using a compound such as $Bu_4NF$, because the $Bu_4N$ cation which remains as by-product may render the activator anion less effective. Most preferably the HF adduct of such a tertiary amine is used which corresponds to the desired ammonium ion of the activator compound. For example, triethylamine would give a triethylammonium cation. Typically, the adduct comprises from 1 to 3 mole of HF per mole of amine, preferably 2.

The product complex is preferably subjected to a cation exchange reaction with a further complex compound comprising a cation capable of reacting with a transition metal compound to form a catalytically active transition metal complex, and a charge balancing anion, wherein the cation and anion are contained in such relative quantities to provide a neutral complex compound. The cation capable of reacting with a transition metal compound to form a catalytically active transition metal complex is preferably selected from the group of Bronsted acidic cations, carbonium cations, silylium cations, and cationic oxidizing agents. The charge balancing anion preferably is a halide, sulphate, nitrate, or phosphate.

The complex compounds used in the cation exchange reaction are known compounds or can be prepared according to conventional processes. The cation exchange may be carried out in a suspension or solution or over a cation exchange column. The cation exchange reaction and the removal of the optional protective groups Pr may be carried out simultaneously.

The product of the cation exchange reaction is recovered, for example by decantation or filtration, and washed with preferably a hydrocarbon. Subsequently, the product complex may be dried using conventional methods, such as applying reduced pressure, heat, employing solvent absorbents, or a combination of these.

All reactions are preferably carried out under an inert atmosphere in the absence of oxygen and moisture.

The compounds $M^{'m+}Q_m$ are known compounds, or can be prepared according to conventional methods. The compounds of formula $Z^1(G_q(T—Bl)_r)$ are typically prepared by reacting $X^{}(G_q(T—Bl)_r)$ or $H(Gq(T—Bl)_r)$, wherein $X^{}$ has the same definition as given hereinbefore, H is hydrogen and T—Bl is T—H or a protected T—H group, with $M^{**}$ or $M^*$, respectively, wherein $M^{**}$ and $M^*$ are a Group 2 element and Group 1 element, respectively. The starting compounds $X^{**}(G_q(T—Bl)_r)$ and $H(G_q(T—Bl)_r)$ can be prepared according to conventional organic synthesis methods.

Having described the invention the following examples are provided as further illustration thereof and are not to be construed as limiting. Unless stated to the contrary all parts and percentages are expressed on a weight basis.

EXAMPLES

The bulk density of the polymers produced in the present examples was determined according to ASTM 1895. The aluminum content on the support material was determined by treatment with sulfuric acid, followed by EDTA addition and back-titration with zinc chloride, as described above.

Example 1

Preparation of activator

A. To a solution of 4-$BrMg(C_6H_4)OSiMe_3$ (ca. 20 mmol, prepared according to the procedure described in J. Org. Chem., 25, 1063, (1960), but using 1,2-dibromoethane instead of methyl iodide to initiate the reaction) in tetrahydrofuran (20 mL) was added slowly, with vigorous stirring, a solution of tris(pentafluorophenyl)borane (4.3 grams, 8.4 mmol) in hexane (200 mL). A viscous solid separated, and the mixture was stirred for 16 hours. The top layer was then decanted from the solid and the residue washed with two 200 mL portions of hexane. The residue was dried under vacuum for 16 hours to yield a pale yellow microcrystalline solid. The solid was quenched with a solution of triethylammonium chloride in distilled water (85 mmol in 200 mL) and the mixture stirred for 1 hour. The solution was decanted from the solid and the residue treated with a second portion of triethylammonium chloride in distilled water (85 mmol in 200 mL). After stirring 1 hour the solution was decanted and the solid washed with two 200 mL portions of distilled water. The residue was dissolved in a mixture of methanol (80 mL) and water (4 mL) and stirred for 16 hours. The solvents were then removed under reduced pressure and the solid dried under vacuum for 16 hours to yield 3.6 grams (60% yield based on tris(pentafluorophenyl)borane) of a very pale yellow microcrystalline solid. The solid as analyzed by $^{13}C$ and $^{19}F$ NMR spectroscopy was found to be triethylammonium tris(pentafluorophenyl)(4-hydroxyphenyl)borate $[NEt_3H][(HOC_6H_4)B(C_6F_5)_3]$. The NMR data indicated the compound to be 95% pure. $^{19}F$ NMR (tetrahydrofuran, ppm): −127.1 (doublet, 2F, ortho); −163.8 (triplet, 1F, para); −165.9 (triplet, 2F, meta). $^{13}C$ NMR (tetrahydrofuran d-8, ppm): 150.5, J=235 Hz; 138.7, J=230 Hz; 140.0, J=245 Hz; 130, broad; 155.8; 135.8; 115.0; 49.0; 11.0.

B. To a solution of 28.7 g (0.16 mol) p-bromophenol and 25.0 g (0.17 mol) t-butyldimethylsilyl chloride in THF was added 35 mL (0.25 mol) triethylamine. A white precipitate was formed and the mixture was refluxed. After 4 hours a sample was analyzed by GCMS (Gas Chromatography Mass Spectroscopy) and this indicated that the reaction was complete. The precipitate was removed by filtration and washed with THF. The THF was evaporated from the filtrate and the resulting orange-brown oil distilled under vacuum to yield 44.1 g (93%) of a colorless liquid having a boiling point of 75° C. to 76° C. at 0.15 mm Hg. GCMS showed the product 4-bromophenoxy-t-butyldimethylsilane to be over 99% pure.

A solution containing 92 mmol t-BuMe$_2$SiOC$_6$H$_4$MgBr was prepared from 26.4 gram (92 mmol) t-BuMe$_2$SiOC$_6$H$_4$Br and 2.7 gram (110 mmol) Mg in 100 mL THF. The Grignard solution was decanted from the excess Mg. About 37 mmol of B(C$_6$F$_5$)$_3$ was dissolved in THF (100 mL) and the resulting solution added to the solution of the Grignard reagent. The clear homogeneous solution was warmed for 40 minutes on an 80° C. waterbath. $^{19}$F NMR analysis indicated a quantitative conversion to the desired borate.

The reaction mixture was cooled to room temperature and a solution of 33 gram (250 mmol) Et$_3$NHCl in water was added. The THF was evaporated until the water began to distill. Then, dichloromethane (200 mL) was added and the water phase separated. The dichloromethane phase was washed with two 100 mL portions of water and two 100 mL portions of water containing CO$_2$ (solid CO$_2$ was added to the two phase system until the pH was 7). The dichloromethane solution was dried over sodium sulphate, filtered and evaporated, resulting in an oil. Yield 45 gram. A $^1$H NMR spectrum of this material showed the presence of t-BuMe$_2$SiOC$_6$H$_4$B(C$_6$F$_5$)$_3$.Et$_3$NH and t-BuMe$_2$SiOC$_6$H$_5$ in about a 1:1 molar ratio. The oil was stirred with pentane (100 mL) for 15 minutes. The pentane was decanted and the procedure repeated with another three 100 mL portions of pentane. The resulting oil was dried in vacuo (0.1 mbar) to yield a beige foam. The yield was 33 gram (quantitative). $^1$H and $^{19}$F NMR spectra indicated the material to be almost pure t-BuMe$_2$SiOC$_6$H$_4$B(C$_6$F$_5$)$_3$.Et$_3$NH.

17 gram (20.7 mmol) of this product was dissolved in THF (100 mL). To this solution, a mixture of Et$_3$N.3HF (5 gram, 31.3 mmol) and Et$_3$N (3.1 gram, 31.3 mmol) was added (effectively Et$_3$N.2HF). After 14 hours $^1$H and $^{19}$F NMR of the whole mixture showed that deprotection was complete and that no side products were formed. The THF was evaporated and to the residue was added 100 mL of 0.5M NaOH and 200 mL of diethylether. The aqueous phase was separated and the ether washed with three 50 mL portions of 0.5M NaOH, two 50 mL portions of water and two 50 mL portions of water containing CO$_2$. The ether was dried over sodium sulphate, filtered and evaporated. The residue was dissolved in 50 mL of dichloromethane and again evaporated (repeated three times). The resulting beige foam was dried in vacuo (0.1 mbar) overnight which yielded 12.8 g of HOC$_6$H$_4$B(C$_6$F$_5$)$_3$.Et$_3$NH (about 90% yield based on B(C$_6$F$_5$)$_3$). $^1$H and $^{19}$F NMR spectra showed the compound to be pure. $^{19}$F NMR (solvent THF-d$_8$) ppm: –126.5 (doublet, 2F, ortho); –163.0 (triplet, 1F, para); –165.5 (doublet, 2F, meta). $^1$H NMR (solvent THF-d$_8$): 1.25 (triplet, 9H); 3.15 (quartet, 6H); 6.35; 7.05 (AB, 4H); 7.05 (broad, 2H).

C. The starting compound 4-bromo-N-methylaminobenzene was synthesized from N-methylaminobenzene according to Organic Syntheses, Vol. 55, p. 20–24.

The next step in the synthesis method is a modified version of that given in J. Org. Chem., 40, 1090, 1975. To a solution of 18.6 g (0.1 mole) 4-bromo-N-methylaminobenzene in 200 mL THF was added at 0° C. a solution of 67 mL of 1.5 molar n-butyllithium in hexane. A pale yellow precipitate was formed. After 10 minutes a solution of 15.1 g (0.1 mole) of t-butyldimethylsilyl chloride in 20 mL THF was added. The temperature of the reaction mixture was allowed to rise to room temperature and the mixture was then refluxed for 6 hours. The solvents were evaporated and distillation of the residue gave 2.0 g (93%) of a yellow liquid 4-bromo-N-t-butyldimethylsilyl-N-methylaminobenzene at a distillation temperature of 100° C. to 110° C. at 0.3 mm Hg. The purity as determined by GCMS was at least 99.5%.

To 2.4 g (0.1 mole) magnesium turnings was added approximately 10% of a solution of 28.0 g (93 mmole) of 4-bromo-N-t-butyldimethylsilyl-N-methylaminobenzene in 100 mL THF. 1,2-dibromoethane (100 μl) was added and the reaction was started by warming up to reflux temperature. The rest of the aniline solution was added in 40 minutes and the mixture was heated at regular times to keep the reaction going. After addition was complete the mixture was refluxed during 2 hours. A sample was quenched with water and analyzed by GCMS: main peak: M=221 (N-t-butyldimethylsilyl-N-methylaminobenzene).

To the THF solution of Grignard reagent was added at room temperature with vigorous stirring 780 mL of a solution containing 31.2 mmole tris(pentafluorophenyl) boron in heptane. The reaction mixture was stirred for 16 hours at room temperature. A viscous material separated. The top layer was decanted and the precipitate was washed with three portions of 100 mL hexane. The residue was dried under vacuum (0.1 mm Hg) for a few hours to yield a white foam. This product magnesiumbromide(4-N-t-butyldimethylsilyl-N-methylaminophenyl)-tris (pentafluorophenyl)borate was used for the next step without further purification.

To the reaction product of the previous step was added a solution of 60 g triethylammonium chloride in 100 mL demineralized water. The mixture was stirred for 2 hours and a homogeneous emulsion formed. The reaction mixture was extracted with four portions of 50 mL dichloromethane and the combined dichloromethane extracts were washed three times with 50 mL demineralized water. The dichloromethane was dried over magnesium sulphate. Filtration and evaporation of the solvent gave the product triethylammonium (4-N-t-butyldimethylsilyl-N-methylaminophenyl)-tris(pentafluorophenyl)borate.

The product of the previous reaction step was dissolved in a mixture of 150 mL methanol, 50 mL water and 2 g triethylammonium chloride and was stirred for 16 hours at room temperature. The methanol was evaporated and 100 mL demineralized water was added to the residue. The suspension was extracted with four portions of 30 mL dichloromethane and the combined dichloromethane extracts were dried over magnesium sulphate. After filtration and evaporation of the solvent 19.6 g (76%) of a dark brown powder remained. For further purification the product was washed three times with toluene. To remove the last traces of toluene the material was mixed two times with 40 mL dichloromethane and the solvent was evaporated. In the course of this treatment the material became less soluble in this solvent. For the last purification step the product was mixed with 100 mL dichloromethane and heated. After cooling, the material was filtered over a Buchner funnel to give after drying in vacuo 12.8 g (50%) of the pure product triethylammonium (4-N-methylaminophenyl)tris-(pentafluorophenyl)borate.

$^1$H-NMR (THF-d$_8$ and acetone-d$_6$): 1.20 (triplet, 9H); 2.70 (singlet, 3H); 3.10 (quartet, 6H); 5.90 (broad, 2H); 6.35; 7.15 (AB, 4H).

$^{13}$C-NMR (THF-d$_8$): 148.9 (J=238); 138.3 (J=233); 136.9 (J=263); 129.0 (broad); 146.5; 134.2; 111.8; 47.1; 31.0; 9.0.

$^{19}$F-NMR (THF-d$_8$+benzene-d$_6$): −127.0 (doublet, 2F, ortho); −163.0 (triplet, 1F, para); −165.5 (triplet, 2F, meta).

D. Analogous to the procedure in Example 1A, triethylammonium tris(pentafluorophenyl) (4-hydroxymethylphenyl) borate was prepared using 4-MgBr(C$_6$H$_4$)CH$_2$OSi(t-Bu)Me$_2$ prepared by reacting 4-bromobenzylalcohol with t-BuMe$_2$SiCl, and converting the reaction product with magnesium into the Grignard reagent.

E. HCl salts of the amines trioctylamine, dimethyl-n-octylamine, dimethylphenylamine, and benzyldimethylamine were quantitatively prepared by leading hydrogen chloride gas through a diethylether solution of the amine until the pH remained acidic (approximately 5 minutes). The solid material was, in each case isolated by filtration, washed with diethylether and dried under vacuum.

Triethylammonium tris(pentafluorophenyl)(4-hydroxylphenyl)borate (1.4 gram, 2 mmol) was dissolved in 25 mL of dichloromethane. An ion exchange reaction was performed by shaking this solution six times with a solution of 4 mmol of the respective HCl salt of the above amines in 20 mL water. The dichloromethane solution was washed five times with portions of 20 mL water and then dried over magnesium sulphate. The mixture was filtered, and the filtrate evaporated to dryness under vacuum to afford the appropriate ammonium salt. The yield in each case was 90% and multinuclear NMR spectroscopy was in full agreement with the proposed structures.

Example 2
Preparation of Support Material Treated With Aluminum Component

A. A 250 mL flask was charged with 5 g of granular silica SD 3216.30 (having a specific surface area of about 300 m$^2$/g, a pore volume of about 1.5 cc/g, and an average particle size of 45 micrometers) available from Grace GmbH, which had been heated at 250° C. for 3 hours under vacuum to give a final water content of less than 0.1 percent by weight as determined by differential scanning calorimetry. 101 g of a 10 weight percent solution of methylalumoxane (MAO) in toluene, available from Witco GmbH, was added and the mixture stirred for 16 hours at room temperature. After this time the toluene was removed under reduced pressure at 20° C., and the solids were dried under vacuum for 16 hours at 20° C. to yield a free flowing powder. The powder was heated at 175° C. for two hours under vacuum. The powder was reslurried in toluene (130 mL) and the mixture heated to 90° C. and stirred for 1 hour. The mixture was filtered and the resulting solid washed with two 50 mL portions of fresh toluene at 90° C. The support was then dried under vacuum at 120° C. for 1 hour. 11.1 g of support was obtained having an aluminum content of 23.8%.

B. A 250 mL flask was charged with 5 g of granular silica SD 3216.30 available from Grace GmbH which had been heated at 250° C. for 3 hours under vacuum to give a final water content of less than 0.1 percent by weight as determined by differential scanning calorimetry. 101 g of a 10 weight percent solution of MAO in toluene was added and the mixture stirred for 16 hours, The solid material was isolated by filtration and then reslurried in toluene (80 mL) and the mixture heated to 90° C. and stirred for 1 hour. The mixture was filtered and the resulting solid washed with two 50 mL portions of fresh toluene at 90° C. The support was then dried under vacuum at 120° C. for 1 hour. 6.7 g of support was obtained having an aluminum content of 13.6%.

C. A 250 mL flask was charged with 5 g of granular silica SD 3216.30 available from Grace GmbH, containing 2.8% of water, and 101 g of a 10 weight percent solution of MAO in toluene was added and the mixture stirred for 16 hours. The solid material was isolated by decantation and then reslurried in toluene (80 mL) and the mixture heated to 90° C. and stirred for 1 hour. The mixture was filtered and the resulting solid washed with two 50 mL portions of fresh toluene at 90° C. The support was then dried under vacuum at 120° C. for 1 hour. 7.3 g of support was obtained having an aluminum content of 15.4%.

D. A 250 mL flask was charged with 10 g of granular silica SD 3216.30 available from Grace GmbH which had been heated at 250° C. for 3 hours under vacuum to give a final water content of less than 0.1 percent by weight as determined by differential scanning calorimetry. 36 g of a 10 weight percent solution of MAO in toluene was added and the mixture stirred for 16 hours. The solid material was isolated by filtration and then reslurried in toluene (100 mL) and the mixture heated to 90° C. and stirred for 1 hour. The mixture was filtered and the resulting solid washed with two 50 mL portions of fresh toluene at 90° C. The support was then dried under vacuum at 120° C. for 1 hour. 13.1 g of support was obtained having an aluminum content of 12.3%.

E. A 250 mL flask was charged with 10 g of granular silica SD 3216.30 available from Grace GmbH which had been heated at 250° C. for 3 hours under vacuum to give a final water content of less than 0.1 percent by weight as determined by differential scanning calorimetry. 72 g of a 10 weight percent solution of MAO in toluene was added and the mixture stirred for 16 hours. The solid material was isolated by filtration and then reslurried in toluene (100 mL) and the mixture heated to 90° C. and stirred for 1 hour. The mixture was filtered and the resulting solid washed with two 50 mL portions of fresh toluene at 90° C. The support was then dried under vacuum at 120° C. for 1 hour. 13.3 g of support was obtained having an aluminum content of 11.4%.

F. A 250 mL flask was charged with toluene (50 mL) and trimethylaluminum (13.5 mL, 0.141 mol). 5 Gram of silica SP-9-10046 (available from Grace Davison) having a water content of 4.5% by weight, based on the combined weights of water and support, was added and the mixture stirred 16 hours. The mixture was filtered and the support washed with toluene (50 mL, about 100° C.) and dried under high vacuum. 5.2 Gram of support was obtained of an aluminum content 7.3% by weight.

G. A 250 mL flask was charged with toluene (50 mL) and triethylaluminum (11 mL, 0.08 mol). 6.3 Gram of silica SP-9-10046 having a water content 4.5% by weight was added and the mixture stirred 1 hour. The mixture was filtered and the support washed with toluene (50 mL, about 100° C.) and dried under high vacuum. 6.3 Gram of support was obtained of an aluminum content of 5.3% by weight.

H. A 250 mL flask was charged with toluene (50 mL) and triethylaluminum (7 mL, 0.051 mol). 5 Gram of silica SP-9-10046 which had been treated at 250° C. for 3 hours under vacuum was added and the mixture stirred 16 hours. The mixture was filtered and the support washed with toluene (50 mL, about 100° C.) and dried under high vacuum. 5.1 Gram of support was obtained of an aluminum content 4.7% by weight.

Preparation of Supported Catalyst

Example 3

Two gram of the support treated as described in Example 2A was slurried in toluene (20 mL) and to this was added triethylammonium tris(pentafluorophenyl)(4-hydroxyphenyl)borate prepared in Example 1 (0.224 g, 0.32 mmol) in toluene (10 mL). The mixture was stirred for 16 hours and then filtered and washed with toluene (3×10 mL) and dried under vacuum at 20° C. 1 g of the solid was slurried in toluene (15 mL) and the mixture stirred for a few minutes. A 0.56 mL aliquot of a dark orange-brown 0.0714M solution (40 micromol) of [(tert-butylamido)(dimethyl)(tetramethyl-$\eta^5$-cyclopentadienyl)silane] dimethyl titanium (hereinafter MCpTi) in ISOPAR™ E (trademark of Exxon Chemical Company) solution was added and the mixture stirred for a few minutes, filtered, washed with toluene (2×10 mL) and dried under vacuum to give a bright yellow colored supported catalyst. The supported catalyst was reslurried in 10 mL of hexane for use in a slurry polymerization reaction.

Example 4

0.5 gram of the support treated as described in Example 2A was slurried in toluene (10 mL) and stirred for a few minutes. This slurry was added to a mixture of triethylammonium tris(pentafluorophenyl)(4-hydroxyphenyl)borate prepared in Example 1 (0.042 g, 60 micromol) in toluene (10 mL) and the mixture stirred for 16 hours. The solids were filtered and washed with 2×10 mL toluene and reslurried in toluene (10 mL). 20 Micromol of MCpTi in ISOPAR™ E was added to give a yellow-brown colored solid phase and a colorless supernatant. The mixture was stirred for a few minutes before use in a polymerization reaction.

Example 5

The procedure of Example 4 was repeated except that 0.028 gram (40 micromol) of triethylammonium tris(pentafluorophenyl)(4-hydroxyphenyl)borate was employed. A supported catalyst consisting of a yellow-brown solid phase and a colorless supernatant was obtained.

Example 6

The procedure of Example 4 was repeated except that 0.014 gram (20 micromol) of triethylammonium tris(pentafluorophenyl)(4-hydroxyphenyl)borate was employed. A supported catalyst consisting of a yellow-brown solid phase and a colorless supernatant was obtained.

Example 7

0.25 gram of the support treated as described in Example 2B was slurried in toluene (5 mL) and stirred for a few minutes. This slurry was added to a mixture of triethylammonium tris(pentafluorophenyl)(4-hydroxyphenyl)borate (0.014 g, 20 micromol) in toluene (5 mL) and the mixture stirred for 16 hours. The toluene was removed by filtration and the solids were washed with 2×10 mL toluene and reslurried in toluene (10 mL). 10 Micromol of MCpTi in ISOPAR™ E was added and the mixture stirred for a few minutes before use in a polymerization reaction. A supported catalyst consisting of a yellow-brown solid phase and a colorless supernatant was obtained.

Example 8

The procedure of Example 7 was repeated except that prior to addition of the transition metal compound the supported catalyst component comprising the treated silica and the triethylammonium tris(pentafluorophenyl)(4-hydroxyphenyl)borate was not washed with toluene.

Example 9

The procedure of Example 7 was repeated except that prior to the addition of the transition metal compound the supported catalyst component comprising the treated silica and the triethylammonium tris(pentafluorophenyl)(4-hydroxyphenyl)borate was not washed with toluene. Also 0.028 g (40 micromol) instead of 0.014 g of triethylammonium tris(pentafluorophenyl)(4-hydroxyphenyl)borate was used.

Example 10

The procedure of Example 9 was repeated except that half of the amount of the final supported catalyst, containing about 5 micromol of MCpTi, was used in a polymerization reaction.

Example 11

The procedure of Example 9 was repeated except that the support treated as in Example 2C. was used.

Example 12

The procedure of Example 9 was repeated except that the support treated as in Example 2D was used.

Examples 13 and 14

The procedure of Example 9 was repeated except that the support treated as in Example 2E was used.

Examples 15 and 16

The procedure of Example 9 was repeated except that the support treated as in Example 2E was used and 0.021 g (30 micromol) of triethylammonium tris(pentafluorophenyl)(4-hydroxyphenyl)borate was used.

Example 17

0.25 Gram of the support treated as described in Example 2E was slurried in toluene (5 mL) and stirred for a few minutes. 10 micromol of MCpTi in ISOPAR™ E was added and the mixture stirred for 15 minutes. The mixture was added to 0.028 g (40 micromol) of triethylammonium tris(pentafluorophenyl)(4-hydroxyphenyl)borate in toluene (10 mL) and the mixture stirred 16 hours to yield a supported catalyst comprising a yellow-brown solid phase and a colorless supernatant.

Example 18

0.014 g (20 micromol) of triethylammonium tris(pentafluorophenyl)(4-hydroxyphenyl)borate was added to toluene (10 mL) and the mixture stirred for a few minutes. 20 micromol of MCpTi in ISOPAR™ E was added and the mixture stirred for 30 minutes. The color changed from yellow to red. 0.5 Gram of the support treated as described in Example 2A in toluene (10 mL) was added and the mixture stirred for 16 hours.

Example 19

Preparation of Supported Catalysts 1.5 gram of the supported catalyst components prepared in Examples 2F (Example 19A), 2.G (Example 19B), and 2.H (Example 19C) was slurried in toluene (20 mL) and the mixture stirred for a few minutes to disperse the support. The slurry was added to a solution of triethylammonium tris(pentafluorophenyl)(4-hydroxyphenyl)borate (0.084 g, 0.120 mmol) in toluene (60 mL) which had been preheated to a temperature of 65° C. to 70° C. The mixture was stirred for 30 minutes at this temperature and then the heating was discontinued and the mixture allowed to cool to ambient temperature. Stirring was continued for an additional 16 hours. A 0.84 mL aliquot of a dark violet 0.0714M solution (60 micromol) of titanium, (N-1,1-dimethylethyl)dimethyl (1-(1,2,3,4,5,-eta)-2,3,4,5-tetramethyl-2,4-cyclopentadien-1-yl)silanaminato))(2-)N)-($\eta^4$-1,3-pentadiene) (hereinafter MCpTi(II)) in ISOPAR™ E (trademark of Exxon Chemical Company) was added and the mixture stirred for about 1 hour to yield a green colored supported catalyst. The catalyst was used as such in a slurry polymerization.

Example 20
Preparation of Supported Catalyst

Triethylammonium tris(pentafluorophenyl)(4-hydroxyphenyl)borate (0.0707 g, 0.1 mmol) was dissolved in toluene (100 mL) by heating the mixture at 70° C. for 15 minutes. A solution of triethylaluminum (50 mL of a 0.002M solution in toluene, 0.1 mmol) was added and the mixture stirred for 5 minutes. 1 Gram of silica SP-9-10046 which had been treated at 250° C. for 3 hours under vacuum was slurried in toluene (20 mL) for 15 minutes and then this slurry was added to the borate/triethylaluminum adduct solution and the mixture was stirred for 5 minutes at a temperature of 70° C. Triethylaluminum (0.24 mL, 2 mmol) was added and the mixture stirred for an additional 5 minutes at 70° C. The mixture was filtered and the support washed once with toluene (100 mL, 70° C.) and twice with 100 mL of boiling hexane. The support was then dried under reduced pressure. 0.25 Gram of the support was slurried in hexane (10 mL) and 0.14 mL of a 0.0714M solution of MCpTi(II) (10 micromol) in hexane was added. The mixture was stirred for 16 hours to yield a supported catalyst consisting of a green solid phase and a colorless supernatant. The catalyst was used as such in a slurry polymerization.

Example 21
Preparation of Supported Catalyst 1.5 Gram of a pretreated support prepared as in Example 2H was slurried in toluene (20 mL) for a few minutes to disperse the support. The slurry was added to a mixture of triethylammonium tris(pentafluorophenyl)(4-((N-methyl)amino)phenyl)borate (0.087 g, 0.120 mmol) in toluene (40 mL) which was preheated to a temperature of 65° C. to 70° C. The mixture was stirred for 30 minutes at this temperature and then the heating was removed and the mixture allowed to cool to ambient temperature. Stirring was continued a further 16 hours. A 0.84 mL aliquot of a 0.0714M solution (60 micromol) of MCpTi(II) in hexane was added and the mixture stirred for about 16 hours to yield a green/brown colored supported catalyst. The catalyst was used as such in a slurry polymerization.

Example 22
Preparation of Supported Catalyst

30 Gram of SiO$_2$ SP-9-10046 treated at 250° C. for 2 hours under vacuum was slurried in toluene (300 mL) and a solution of triethylaluminum (30 mL, 0.22 mol) in toluene (200 mL) was added. The mixture was stirred for 1 hour, filtered, washed with two 100 mL portions of fresh toluene and dried under vacuum. To 20 gram of the resulting powder was added toluene (200 mL). The mixture was stirred for a few minutes to disperse the support. This slurry was added to a solution of triethylammonium tris(pentafluorophenyl)(4-hydroxyphenyl)borate (1.125 gram, 1.6 mmol) in toluene (200 mL) which had been heated to 70° C. and kept at 70° C. for 30 minutes. Upon addition, the heating was removed and the mixture stirred at ambient temperature for 16 hour. A 40 mL aliquot of the resulting slurry (containing approximately 1 gram of the support) was withdrawn and to this was added 0.47 mL of a 0.0855M solution of bis (indenyl)zirconium dimethyl (Witco GmbH) (40 micromol of Zr). The mixture was stirred for a few minutes to yield an orange colored supported catalyst. An aliquot of this supported catalyst containing 14 micromol of zirconium was used as such in a slurry polymerization.

Example 23
Preparation of Supported catalyst 20 gram of SiO$_2$ (SP-9-10046) treated at 250° C. for 2 hours under vacuum was slurried in toluene (300 mL) and triethylaluminum (20 mL, 0.147 mol) was added. The mixture was stirred for 1 hour, filtered, washed with two 100 mL portions of fresh toluene and dried under vacuum. To 1.5 gram of the resulting powder was added toluene (20 mL). The mixture was stirred for a few minutes to disperse the support. This slurry was added to a solution of triethylammonium tris(pentafluorophenyl)(4-hydroxymethylphenyl)borate (0.086 gram 0.12 mmol) in toluene (40 mL), which had been heated to 70° C., and kept at 70° C. for 1 hour. Upon addition, the heating was removed and the mixture stirred at ambient temperature for 16 hours. 0.84 mL of a 0.0714M solution of MCpTi(II) (60 micromol Ti) was added and the mixture was stirred for a 1 hour to yield a green-brown colored supported catalyst. An aliquot of this supported catalyst containing 10 micromol of titanium was used as such in a slurry polymerization.

Example 24
Slurry Phase Ethylene/1-octene Copolymerization

A catalyst was prepared as in Example 19C. 20 Micromol of catalyst, based on titanium, was used in a slurry polymerization. 250 mL of 1-octene was added to the reactor. An ethylene/1-octene copolymer of density 0.9376 g/cm$^3$ was prepared.

Example 25-26
Preparation of supported catalyst

30 Gram of SiO$_2$ (SP-9-10046) treated at 250° C. for 2 hours under vacuum was slurried in toluene (300 mL) and triethylaluminum (30 mL, 0.22 mol) was added. The mixture was stirred for 1 hour, filtered, washed with two 100 mL portions of fresh toluene and dried under vacuum.

To 3 gram of the resulting powder was added toluene (20 mL). The mixture was stirred for a few minutes to disperse the support. This slurry was added to a solution of triethylammonium tris(pentafluorophenyl)(4-hydroxyphenyl)borate (0.126 g, 0.18 mmol) in toluene (40 mL) which had been heated to 80° C. and kept at 80° C. for 1 hour. Upon addition, the heating was discontinued and the mixture stirred at ambient temperature for 16 hours. 1.68 mL of 0.0714M solution of MCpTi(II) was added and the mixture was stirred for 1 hour to yield a green colored supported catalyst.

Another 3 gram portion of the resulting powder was treated according to the same procedure, yet using 0.105 gram, 0.15 mmol of borate which had been heated to 70° C. and kept at 70° C. for 1 hour.

Aliquots of the resulting supported catalysts containing 10 micromol of titanium were used as such in a slurry polymerization.

Comparative Example 1

0.5 gram of silica SD 3216.30 (dehydrated for 3 hours at 250° C. under vacuum) was slurried in toluene (10 mL), stirred for a few minutes and then added to triethylammonium tris(pentafluorophenyl)(4-hydroxyphenyl)borate (0.028 gram, 40 micromol) in toluene (10 mL) and the mixture stirred for 16 hours. 20 micromol of MCpTi in ISOPAR™ E was added to give a pale yellow solid phase and a colorless supernatant.

Comparative Example 2

Triethylammonium tris(pentafluorophenyl)(4-hydroxyphenyl)borate (0.014 gram, 20 micromol) in 10 mL of toluene was treated with 20 micromol of MCpTi in ISOPAR™ E. The resulting red colored mixture was stirred for a few minutes and then used as such in a polymerization reaction.

Example 27

Polymerization Runs

A 10 liter autoclave reactor was charged with 6 liter anhydrous hexane, 1 liter of hydrogen gas, and the reactor contents heated to 80° C., unless indicated otherwise, at which temperature the polymerization mixture was maintained during polymerization. Ethylene was then added in order to raise the pressure to the desired operating level of 10 bar, unless indicated otherwise. A sample of supported catalyst as prepared in the previous examples and comparative examples was added to the reactor through a pressurized addition cylinder in the amounts indicated in the table below. Ethylene was supplied to the reactor continuously to keep the pressure constant. After the desired reaction time the ethylene line was blocked and the reactor contents were dumped to a sample container. The hexane was removed from the polymer and the polymer dried overnight and then weighed to determine catalyst efficiencies. In none of the inventive examples did substantial reactor fouling occur and all examples gave a polymer in a free flowing powder form.

The table summarizes the specific conditions and the results of slurry polymerizations with the above prepared supported catalyst.

Example 28

Continuous Slurry Phase Polymerizations 20 gram of triethylaluminum treated $SiO_2$ (prepared as in Example 22) was slurried in toluene (200 mL) and the mixture heated to 80° C. In a separate vessel, triethylammonium tris(pentafluorophenyl)(4-hydroxyphenyl)borate (1.125 gram, 1.6 mmol) was added to toluene (400 mL) and the mixture heated to 80° C. and kept at 80° C. for 1 hour. The borate solution was added to the support slurry and the mixture stirred and kept at 80° C. for 2 hours. The mixture was cooled and stirred overnight. The toluene was decanted from the support and replaced with hexane (800 mL). This procedure was repeated. 8 mmol of MMAO type 3A (20 weight percent solution in heptane from AKZO) was added and the mixture stirred for 15 minutes. 11.2 mL of a 0.0714M solution of MCpTi(II) was added and the mixture stirred for 2 hours before use. The support contained a boron loading of 80 micromol/g and a titanium loading of 40 micromol/g.

Isopentane, ethylene, 1-butene (if required), hydrogen, and supported catalyst were continuously fed into a 10 L jacketed, continuously stirred tank reactor and the slurry product formed was removed continuously. The total pressure in all polymerization runs was 15 bar and the temperature was maintained at 70° C. The slurry withdrawn was fed to a flash tank to remove the diluent and the dry, free-flowing polymer powder was collected. In a first run the following conditions were used: isopentane flow of 29500 g/hour; ethylene flow of 1,200 g/hour; hydrogen flow of 0.4 1/hour; temperature of 70° C. to produce a product having a bulk density of 0.354 g/cm$^3$, and a melt flow index, measured at 190° C. and a load of 21.6 kg of 1.4 g/10 minutes, with an efficiency of 1,500,000 g PE/g Ti. In a second run the following conditions were used: isopentane flow of 2,500 g/hr; ethylene flow of 800 g/hour; butene flow of 42.5 g/hr; hydrogen flow of 0.45 1/hour; temperature of 70° C. to produce a product having a bulk density of 0.300 g/cm$^3$, a density of 0.9278 g/cm$^3$, a butene content of 1.42 mol %, and a melt flow index, measured at 190° C. and a load of 2.16 kg of 0.85 g/10 minutes, with an efficiency of 650,000 g PE/g Ti.

Example 29

Solution Phase Polymerizations 30 gram of $SiO_2$ (SP-9-10046) treated at 250° C. for 3 hr under vacuum was slurried in toluene (300 mL) and triethylaluminum (30 mL, 0.22 mol) was added. The mixture was stirred for 1 hour, filtered, washed with two 100 mL portions of fresh toluene and dried under vacuum. To 10 gram of the resulting powder was added toluene (150 mL). The mixture was stirred for a few minutes to disperse the support. This slurry was added to a solution of triethylammonium tris(pentafluorophenyl)(4-hydroxyphenyl)borate (0.565 gram, 0.8 mmol) in toluene (250 mL) which had been heated to 70° C. and kept at 70° C. for 1 hour. Upon addition, the heating was removed and the mixture stirred at ambient temperature for 16 hours. A 50 mL aliquot of the slurry was treated with 0.7 mL of a 0.0714M solution of MCpTi(II) (50 micromol Ti) followed by 500 micromol of MMAO and the mixture was stirred for 1 hour to yield a green-brown colored supported catalyst. Aliquots of this supported catalyst containing 2 and 1.25 micromol of titanium, respectively, were used.

A 3 liter autoclave reactor was charged with the desired amount of 1-octene followed by an amount of ISOPAR™ E sufficient to give a total volume of 1500 mL. 300 mL of hydrogen gas was added and the reactor contents were heated to the desired temperature. Ethylene was then added sufficient to bring the pressure of the system to 30 bar. A supported catalyst was added to initiate the polymerization and ethylene was supplied to the reactor continuously on demand. After 10 minutes the ethylene line was blocked and the reactor contents were dumped into a sample container. The polymer was dried overnight and then weighed to determine catalyst efficiencies. The specific conditions were: Run 1: 121 mL octene; temperature of 130° C.; to give 82 g of product (efficiency 854,000 based on g PE/g Ti) of a melt index (at 190° C./2.16 kg load) of 3.8 and a density of 0.9137. Run 2: 450 mL octene; temperature of 80° C.; to give 47 g of product (efficiency 785,000 based on g PE/g Ti) of a melt index (190° C./2.16 kg) of 1.66 g/10 minutes and a density of 0.8725 g/cm$^3$.

| Catalyst from Ex. No. | [Al] wt. % on support | μmol[b] activator/ g treated support | Activator[b]/ MC$_p$Ti [mol/gatom] | [Ti][b] μmol MCpTi added to reactor | Time (min) | Yield (g) | Efficiency (Ti) (gPE/gTi/hr) | Efficiency (SiO$_2$) (gPE/gSiO$_2$/hr) | Efficiency (Al) (gPE/gAl/hr) | Bulk density (g/cm$^3$) |
|---|---|---|---|---|---|---|---|---|---|---|
| 3 | 23.8 | 160 | 4 | 40 | 45 | 870 | 605,428 | 2,373 | 4,874 | 0.30 |
| 4 | 23.8 | 120 | 3 | 20 | 60 | 865 | 902,923 | 3,540 | 7,269 | 0.30 |
| 5 | 23.8 | 80 | 2 | 20 | 62 | 945 | 954,610 | 3,742 | 7,685 | 0.28 |
| 6 | 23.8 | 40 | 1 | 20 | 30 | 235 | 490,605 | 1,923 | 3,950 | 0.26 |
| 7 | 13.6 | 80 | 2 | 10 | 90 | 660 | 918,580 | 2,486 | 12,941 | 0.29 |
| 8 | 13.6 | 80 | 2 | 10 | 60 | 775 | 1,617,954 | 4,379 | 22,794 | 0.24 |
| 9 | 13.6 | 160 | 4 | 10 | 38 | 1093 | 3,602,981 | 9,752 | 50,759 | 0.24 |
| 10 | 13.6 | 160 | 4 | 5 | 60 | 330 | 1,377,871 | 3,730 | 19,412 | 0.27 |
| 11 | 15.4 | 160 | 4 | 10 | 60 | 980 | 2,045,929 | 5,858 | 25,455 | 0.22 |
| 12 | 12.3 | 160 | 4 | 10 | 60 | 820 | 1,711,900 | 4,458 | 26,667 | 0.22 |
| 13 | 11.4 | 160 | 4 | 10 | 60 | 1140 | 2,379,958 | 6,039 | 40,000 | 0.23 |
| 14 | 11.4 | 160 | 4 | 10 | 50 | 1000 | 2,505,219 | 6,357 | 42,105 | 0.20 |
| 15 | 11.4 | 120 | 3 | 10 | 57 | 1000 | 2,197,561 | 5,576 | 36,934 | 0.21 |
| 16 | 11.4 | 120 | 3 | 10 | 60 | 610 | 1,273,486 | 3,231 | 21,404 | 0.23 |
| 17 | 11.4 | 160 | 4 | 10 | 65 | 620 | 1,194,797 | 3,032 | 20,081 | 0.21 |
| 18[a] | 23.8 | 80 | 2 | 20 | 60 | 190 | 198,330 | 778 | 1597 | 0.26 |
| 19A[c,f] | 7.3 | 80 | 2 | 5 | 45 | 350 | 1,948,500 | 4,413 | 51,141 | 0.21 |
| 19B[d,f] | 5.3 | 80 | 2 | 10 | 66 | 1,105 | 2,097,170 | 4,824 | 75,815 | 0.25 |
| 19C[d,f] | 4.7 | 80 | 2 | 10 | 41 | 460 | 1,405,367 | 3,160 | 57,291 | 0.21 |
| 20[e,f] | n.m. | 100 | 2.5 | 14 | 60 | 450 | 939,457 | n.m | n.m. | 0.26 |
| 21[c,f] | n.m. | 80 | 2 | 10 | 55 | 300 | 683,242 | n.m. | n.m. | 0.18 |
| 22[c,f] | 5.0 | 80 | 2 | 14 | 60 | 470 | 368,916 | 1,594 | 26,857 | 0.17 |
| 23[c,g] | 5.0 | 80 | 2 | 10 | 12 | 200 | 2,087,682 | 4,747 | 80,000 | 0.14 |
| 24[f,h] | 5.3 | 80 | 2 | 20 | 80 | 840 | 657,620 | 1,512 | 23,773 | 0.21 |
| 25[c,f] | 5.0 | 60 | 1.5 | 10 | 20 | 500 | 3,131,524 | 7,121 | 120,000 | 0.24 |
| 26[c,i] | 5.0 | 50 | 1.25 | 10 | 85 | 1570 | 2,313,644 | 5,590 | 88,659 | 0.21 |
| Comp. 1 | 0 | 80 | 2 | 20 | 20 | — | — | — | — | — |
| Comp. 2 | — | | 1 | 20 | 20 | — | — | — | — | — |

[a]The pressure was 15 bar.
[b]All the ratios and amounts given relate to the ratios/amounts used in the preparation of the supported catalysts according to the particular examples.
[c]The temperature was 60° C.
[d]The temperature was 40° C and the pressure 7 bar.
[e]The temperature was 40° C and the pressure 6 bar.
[f]100 micromol of MMAO Type 3A from AKZO was added to the polymerization reactor prior to the catalyst.
[g]300 micromol of MMAO Type 3A from AKZO was added to the polymerization reactor prior to the catalyst.
[h]The temperature was 30° C.
[i]100 micromol of (i-Bu)$_3$Al was added to the polymerization reactor prior to the catalyst.

What is claimed is:

1. A supported catalyst component consisting essentially of:
   (a)(1) a support material, and
   (a)(2) an organometal or metalloid compound wherein the metal or metalloid is selected from the group consisting of magnesium, zinc, boron, aluminum, germanium, tin, lead, and mixtures thereof; and
   (b) an activator compound comprising:
      (b)(1) a cation which is capable of reacting with a transition metal metallocene compound to form a transition metal complex which is catalytically active for the polymerization of alpha-olefins; and
      (b)(2) a compatible anion having up to 100 nonhydrogen atoms and containing at least one substituent comprising a moiety having an active hydrogen.

2. A supported catalyst component according to claim 1 wherein the support material comprises silica.

3. A supported catalyst component according to claim 1 wherein the organometal compound is an aluminum component selected from the group consisting of an alumoxane, an aluminum compound of the general formula $AlR^1_xR^2_y$ wherein $R^1$ independently in each occurrence is hydride, a hydrocarbyl radical, a trihydrocarbylsilyl radical, trihydrocarbyl germyl radical, or a trihydrocarbyl-, trihydrocarbylsilyl-, or trihydrocarbyl germyl substituted metalloid radical, $R^2$ independently is the same as $R^1$, x is 2 or 3, y is 0 or 1 and the sum of x and y is 3, and a combination thereof.

4. A supported catalyst component according to claim 3 wherein the aluminum component is selected from the group consisting of an alumoxane and aluminum compounds of the formula $AlR^1_x$, wherein $R^1$ independently in each occurrence is hydrogen or a hydrocarbyl radical having from 1 to 20 carbon atoms, and x is 3.

5. A supported catalyst component according to claim 1 containing at least a stoichiometric amount of organometal compound, based on the metal therein, with respect to hydroxyl groups present on the support material.

6. A supported catalyst component according to claim 1 wherein in the anion (b)(2) the substituent comprising a moiety having an active hydrogen corresponds to the formula;

$$G_q(T-H)_r$$

wherein G is a polyvalent hydrocarbon radical, T is O, S, NR, or PR, wherein R is a hydrocarbyl radical, a trihydrocarbylsilyl radical, a trihydrocarbyl germyl radical or hydrogen, H is hydrogen, q is 0 or 1, and r is an integer from 1 to 3.

7. A supported catalyst component according to claim 1 wherein the compatible anion portion of the activator compound corresponds to general Formula (I)

$$[M'^{m+}Q_n(G_q(T-H)_r)_z]^{d-} \qquad (I)$$

wherein

M' is a metal or metalloid selected from the group consisting of aluminum, gold, platinum, boron, phosphorus and silicon;

Q independently in each occurrence is selected from the group consisting of hydride, dihydrocarbylamido, halide, hydrocarbyloxide, hydrocarbyl, and hydrocarbyl-substituted organo-metalloid radicals, the hydrocarbyl portion having from 1 to 20 carbons with the proviso that in not more than one occurrence is Q halide;

G is a polyvalent hydrocarbon radical having r+1 valencies bonded to M' and T;

T is O, S, NR, or PR, wherein R is a hydrocarbyl radical, a trihydrocarbylsilyl radical, a trihydrocarbyl germyl radical or hydrogen;

m is an integer from 1 to 7;

n is an integer from 0 to 7;

q is an integer of 0 or 1;

r is an integer from 1 to 3;

z is an integer from 1 to 8;

d is an integer from 1 to 7; and n+z−m=d.

8. A supported catalyst component according to claim 7 wherein the compatible anion is tris(pentafluorophenyl)(4-hydroxyphenyl) borate.

9. A supported catalyst component according to claim 1 wherein the cation (b)(1) is selected from the group consisting of Bronsted acidic cations, carbonium cations, sylium cations, and cationic oxidizing agents.

10. A supported catalyst component according to claim 1 containing from 1 to 2,000 $\mu$mol of activator compound per gram of support material.

11. A supported catalyst comprising the supported catalyst component of claim 1 and (c) a transition metal metallocene compound containing a transition metal from Group 3, 4, 5, 6 or the Lanthanides and containing a substituent which reacts with activator compound (b) to thereby form a transition metal complex which is catalytically active for the polymerization of alpha-olefins.

12. A supported catalyst according to claim 11 wherein the transition metal compound (c) contains at least one π-bonded anionic ligand group which is a conjugated or non-conjugated, cyclic or non-cyclic dienyl group, an allyl group, aryl group, or a substituted derivative thereof.

13. A supported catalyst according to claim 12 wherein the π-bonded anionic ligand group is a cyclopentadienyl group or a derivative thereof.

14. A supported catalyst according to claim 11 wherein the ratio of moles of activator compound (b) to gram-atoms of transition metal in compound (c) is from 0.05:1 to 100:1 mole of (b) per gram-atom of transition metal in (c).

15. A process for preparing a supported catalyst component consisting essentially of combining (a)(1) a support material and (a)(2) an organometal or metalloid compound wherein the metal or metalloid is selected from the group consisting of magnesium, zinc, boron, aluminum, germanium, tin, lead, and mixtures thereof; and (b) an activator compound comprising (b)(1), a cation which is capable of reacting with a transition metallocene compound to form a transition metal complex which is catalytically active for the polymerization of alpha-olefins, and (b)(2) a compatible anion having up to 100 nonhydrogen atoms and containing at least one substituent comprising a moiety having an active hydrogen.

16. A process according to claim 15 comprising the steps of: subjecting the support material to a thermal treatment at 100° C. to 1000° C.; combining the thermally treated support material with the organometal or organometalloid compound in a diluent or solvent; and subsequently combining the resulting product with the activator compound.

17. A process according to claim 15 comprising the steps of: combining the activator compound with the organometal compound to form an adduct; and combining the adduct with the support material.

18. A process according to claim 15 comprising the steps of: combining a water containing support material with the organometal or organometalloid compound; and combining the resulting product with the activator compound.

19. A process for preparing a supported catalyst comprising the process according to claim 15, claim 16, claim 17 or claim 18 and further comprising the step of adding (c) a transition metal metallocene compound containing a transition metal from Group 3, 4, 5, 6 or the Lanthanides and containing a substituent which reacts with activator (b) to thereby form a transition metal complex which is catalytically active for the polymerization of alpha-olefins.

20. The supported catalyst component according to claim 7 wherein the hydrocarbyl portion of a hydrocarbyl or of a hydrocarbyl-substituted organo-metalloid radical is a non-halo-substituted hydrocarbyl or a halo-substituted hydrocarbyl.

21. A process for the preparation of an adduct of (a)(2) an organometal or metalloid compound wherein the metal or metalloid is selected from the group consisting of magnesium, zinc, boron, aluminum, germanium, tin, lead, and mixtures thereof; and an activator compound comprising (b)(1) a cation which is capable of reacting with a transition metal metallocene compound to form a transition metal complex which is catalytically active for the polymerization of alpha olefins and, (b)(2) a compatible anion having up to 100 nonhydrogen atoms and containing at least one substituent comprising a moiety having an active hydrogen, comprising combining the organometal or metalloid compound and the activator compound in a diluent or solvent, optionally followed by removing the solvent or diluent.

22. An adduct of (a)(2) an organometal or metalloid compound wherein the metal or metalloid is selected from the group consisting of magnesium, zinc, boron, aluminum, germanium, tin, lead, and mixtures thereof: and an activator compound comprising (b)(1) a cation which is capable of reacting with a transition metal metallocene compound to form a transition metal complex which is catalytically active for the polymerization of alpha olefins and, (b)(2) a compatible anion having up to 100 nonhydrogen atoms and containing at least one substituent comprising a moiety having an active hydrogen.

23. An adduct according to claim 22 wherein the organometal compound is an aluminum component selected from the group consisting of an alumoxane, an aluminum compound of the general formula $AlR^1_x R^2_y$ wherein $R^1$ independently in each occurrence is hydride, a hydrocarbyl radical, a trihydrocarbylsilyl radical, trihydrocarbyl germyl radical, or a trihydrocarbyl-, trihydrocarbyl silyl-, or trihydrocarbyl germyl substituted metalloid radical, $R^2$ independently is the same as $R^1$, a hydrocarbyloxy radical or a halide radical, x is 2 or 3, y is 0 or 1 and the sum of x and y is 3, and a combination thereof.

24. An adduct according to claim 22 wherein in the anion (b)(2) the substituent comprising a moiety having an active hydrogen corresponds to the formula:

$$G_q(T{-}H)_r$$

wherein G is a polyvalent hydrocarbon radical, T is O, S. NR, or PR, wherein R is a hydrocarbyl radical, a trihydrocarbylsilyl radical, a trihydrocarbyl germyl radical or hydrogen, H is hydrogen, q is 0 or 1, and r is an integer from 1 to 3.

* * * * *

UNITED STATES PATENT AND TRADEMARK OFFICE
CERTIFICATE OF CORRECTION

PATENT NO. : 5,834,393

DATED : November 10, 1998

INVENTOR(S) : Grant Berent Jacobsen, et al.

Page 1 of 2

It is certified that error appears in the above-identified patent and that said Letters Patent is hereby corrected as shown below:

Title Page, column 1, Title, line 3, "COMPONENT SUPPORTED" should correctly read --COMPONENT, SUPPORTED--.

Title Page, column 1, Title, line 4, "CATALYST PROCESSES" should correctly read --CATALYST AND PROCESSES--.

Column 4, line 25, "$[M^{m+}Q_n(G_q(T-Bl)_r)_z]^{d-}$" should correctly read --$[M^{m+}Q_n(G_q(T-Bl)_r)_z]^{d-}$---.

Column 4, line 59, "$[M]+$" should correctly read --$[M]^+$--.

Column 6, line 19, "S—OH+MgR$_2$+S—OMgR+RH" should correctly read -- S—OH+MgR$_2$→S—OMgR+RH--.

Column 9, line 46, "nitrites" should correctly read --nitriles--.

Column 10, line 8, "radicals" should correctly read --radical--.

Column 10, line 44 "(6hydroxy-2-naphthyl)" should correctly read --(6-hydroxy-2-naphthyl)--.

Column 14, line 24, "GeR*2, BR*, or BR*2" should correctly read --$GeR^*_2$, $BR^*$, or $BR^*_2$--.

Column 15, line 3, "and" should correctly read --or--.

Column 15, line 61, "CR*2CR*2," should correctly read --$CR^*_2CR^*_2$,--.

Column 18, line 59, "cis" should correctly read --is--.

Column 19, lines 23 and 26, "in independently" should correctly read --independently--.

Column 22, line 8, "solvents" should correctly read --solvent--.

Column 24, line 36, delete "H".

Column 24, line 45, "Li+, MgCl+, MgBr+, or MgI+" should correctly read --$Li^+$, $MgCl^+$, $MgBr^+$, or $MgI^+$--.

UNITED STATES PATENT AND TRADEMARK OFFICE
CERTIFICATE OF CORRECTION

PATENT NO. : 5,834,393

DATED : November 10, 1998

INVENTOR(S) : Grant Berent Jacobsen, et al.

It is certified that error appears in the above-identified patent and that said Letters Patent is hereby corrected as shown below:

Column 25, line 21, "Pr" should correctly read --B1--.

Column 25, line 60, "Pr" should correctly read --B1--.

Claim 7, column 38, line 63, "$[M^{m+}Q_n(G_q(T{-}H)_r)_z]^{d-}$" should correctly read --$[M^{m+}Q_n(G_q(T\text{-}H)_r)_z]^{d-}$--.

Claim 15, column 39, line 55, "transition metallocene" should correctly read --transition metal metallocene--.

Claim 17, column 40, lines 2-3 "organometal compound" should correctly read --organometal or organometalloid compound--.

Signed and Sealed this

Sixth Day of March, 2001

NICHOLAS P. GODICI

Attest:

Attesting Officer

Acting Director of the United States Patent and Trademark Office